US009175327B2

(12) United States Patent
Kanamori et al.

(10) Patent No.: US 9,175,327 B2

(45) Date of Patent: Nov. 3, 2015

(54) COMPOSITION FOR SYNTHESIZING PROTEIN WITH REDUCED LIPOPOLYSACCHARIDE CONTAMINATION, METHOD FOR PRODUCING PROTEIN USING SAID COMPOSITION

(75) Inventors: Takashi Kanamori, Kashiwa (JP); Yuki Hayami, Kashiwa (JP); Kanehisa Kojoh, Kashiwa (JP); Takuya Ueda, Tokyo (JP); Kumiko Tsuihiji, Kashiwa (JP); Tomoe Fuse, Tokyo (JP); Mikiko Nakamura, Kashiwa (JP); Shizue Kato, Kashiwa (JP)

(73) Assignees: GeneFrontier Corporation, Kashiwa (JP); The University of Tokyo, Tokyo (JP)

( * ) Notice: Subject to any disclaimer, the term of this patent is extended or adjusted under 35 U.S.C. 154(b) by 522 days.

(21) Appl. No.: 13/100,050

(22) Filed: May 3, 2011

(65) Prior Publication Data

US 2012/0231496 A1 Sep. 13, 2012

(30) Foreign Application Priority Data

Mar. 10, 2011 (JP) ................................ 2011-053547

(51) Int. Cl.
*C12P 21/02* (2006.01)
*C12N 15/10* (2006.01)

(52) U.S. Cl.
CPC .................................... *C12P 21/02* (2013.01)

(58) Field of Classification Search
None
See application file for complete search history.

(56) References Cited

U.S. PATENT DOCUMENTS

| | | | | |
|---|---|---|---|---|
| 5,968,767 | A * | 10/1999 | Sheikh et al. | 435/68.1 |
| 2009/0170069 | A1* | 7/2009 | Ghosh et al. | 435/5 |
| 2010/0273240 | A1* | 10/2010 | Sanyal | 435/252.33 |
| 2012/0021922 | A1* | 1/2012 | Pfleger et al. | 506/7 |

FOREIGN PATENT DOCUMENTS

| | | | | |
|---|---|---|---|---|
| JP | 4061043 | B2 | | 3/2008 |
| JP | 2008-271903 | A | | 11/2008 |
| JP | 2008271903 | A | * | 11/2008 |
| WO | 02/53582 | A2 | | 7/2002 |

OTHER PUBLICATIONS

Reichelt et al., 'Single step protocol to purify recombinant proteins with low endotoxin contents'; Protein expression and Purification, vol. 46, pp. 483-488, 2006.*

Machine translation of Ueda et al., JP 2008-271903 A accessed Dec. 7, 2013.*

Lessard et al., Studies on the formation of transfer ribonucleic acid-ribosome complexes; JBC, vol. 247, No. 21, 00. 6909-6912, 1972.*

Anderson, W.F. et al., The effect of tRNA concentration on the rate of protein synthesis; PNAS, vol. 62, No. 2, pp. 566-573, 1969.*

Magalhaes et al., *Journal of Pharmacy and Pharmaceutical Sciences*, 10(3): 388-404 (2007).

Matsuura et al., *Biochemical and Biophysical Research Communications*, 352(2): 372-377 (2007).

Ohashi et al., *Biochemical and Biophysical Research Communications*, 352(1): 270-276 (2007).

Osada et al., *Journal of Biochemistry*, 145(5): 693-700 (2009).

Petsch et al., *Journal of Biotechnology*, 76(2-3): 97-119 (2000).

Reichelt et al., *Protein Expression and Purification*, 46(2): 483-488 (2006).

Shimizu et al., *Methods*, 36(3): 299-304 (2005).

Shimizu et al., *Nature Biotechnology*, 19(8): 751-755 (2001).

Villemagne et al., *Journal of Immunological Methods*, 313(1-2): 140-148 (2006).

Janosi et al., *Proc. Natl. Acad. Sci. USA*, 91: 4249-4253 (May 1994).

Shimizu et al., *Nat. Biotechnol.*, 19: 751-755 and Supplementary Table 1 (Aug. 2001).

BioComber Co., Ltd., "Reconstituted in vitro translation kit PURESYSTEM™ classic II Instruction Manual," pp. 1-21 (Tokyo, Japan) [downloaded from BioComber website (http://www.biocomber.co.jp) on Nov. 25, 2013].

Cammack et al. (eds.), *Oxford Dictionary of Biochemistry* (Oxford University Press 2006), entry for "termination factor" [downloaded from Answers.com on Nov. 25, 2013].

Jabion website entry for "termination factor" [downloaded from http://www.bioportal.jp on Nov. 25, 2013].

Katzen et al., *Trends in Biotechnology*, 23(3): 150-156 (Mar. 2005).

European Patent Office, International Search Report in International Patent Application No. PCT/JP2012/056784 (Jun. 25, 2012).

New England Biolabs, Inc., information printout entitled "The Next Generation of Cell-free Protein Synthesis" (downloaded from https://www.neb.com/tools-and-resources/feature-articles/the-next-generation-of-cell-free-protein-synthesis on Mar. 11, 2014).

New England Biolabs, Inc., PURExpress® In Vitro Protein Synthesis Instruction Manual (Mar. 2013).

* cited by examiner

*Primary Examiner* — Jennifer Dunston
*Assistant Examiner* — Addison D Ault
(74) *Attorney, Agent, or Firm* — Leydig, Voit & Mayer, Ltd.

(57) ABSTRACT

According to the present invention, a composition possessing cell-free protein synthesis activity with reduced contaminating lipopolysaccharide, and a method for producing a protein using the same are provided. When ribosome display is performed using the composition and method for protein production of the present invention, the background that is caused by non-specific binding is reduced, so that a nucleic acid that encodes the desired polypeptide can be selected with high accuracy and high efficiency.

12 Claims, 7 Drawing Sheets

```
                         SEQUENCE LISTING

<160> NUMBER OF SEQ ID NOS: 9

<210> SEQ ID NO 1
<211> LENGTH: 59
<212> TYPE: DNA
<213> ORGANISM: Artificial Sequence
<220> FEATURE:
<223> OTHER INFORMATION: Synthetic 5' primer for ribosomal display

<400> SEQUENCE: 1

atggactata aagatgacga tgacaaaggc caggtgcagc tgttggagtc tgggggagg      59


<210> SEQ ID NO 2
<211> LENGTH: 58
<212> TYPE: DNA
<213> ORGANISM: Artificial Sequence
<220> FEATURE:
<223> OTHER INFORMATION: Synthetic 3' primer for ribosomal display

<400> SEQUENCE: 2

gatggtgacc tccgctgcca ccgaattcca gatcctcttc tgagatgagt ttttgttc       58


<210> SEQ ID NO 3
<211> LENGTH: 112
<212> TYPE: DNA
<213> ORGANISM: Artificial Sequence
<220> FEATURE:
<223> OTHER INFORMATION: Synthetic 5' UTR sequence

<400> SEQUENCE: 3

gaaattaata cgactcacta tagggagacc acaacggttt ccctctagaa ataattttgt     60

ttaactttaa gaaggagata taccaatgga ctataaagat gacgatgaca aa            112


<210> SEQ ID NO 4
<211> LENGTH: 24
<212> TYPE: DNA
<213> ORGANISM: Artificial Sequence
<220> FEATURE:
<223> OTHER INFORMATION: Synthetic primer for g3p gene

<400> SEQUENCE: 4

gaatatcaag gccaatcgtc tgac                                            24


<210> SEQ ID NO 5
<211> LENGTH: 108
<212> TYPE: DNA
<213> ORGANISM: Artificial Sequence
<220> FEATURE:
<223> OTHER INFORMATION: Synthetic primer for g3p gene

<400> SEQUENCE: 5
```

-continued

```
ctcgagttat tcattaggtg aggcgttgag ggccagcacg gatgccttgc gcctggctta     60

tccagacggg cgtgctgaat tttgcgccgg aaacgtcacc aatgaaac                 108


<210> SEQ ID NO 6
<211> LENGTH: 48
<212> TYPE: DNA
<213> ORGANISM: Artificial Sequence
<220> FEATURE:
<223> OTHER INFORMATION: Synthetic primer for erk2-g3p fragment

<400> SEQUENCE: 6

gaaattaata cgactcacta tagggagacc acaacgcttt ccctctag                  48


<210> SEQ ID NO 7
<211> LENGTH: 32
<212> TYPE: DNA
<213> ORGANISM: Artificial Sequence
<220> FEATURE:
<223> OTHER INFORMATION: Synthetic primer for erk2-g3p fragment

<400> SEQUENCE: 7

ggattagtta ttcattaggt gaggcgttga gg                                   32


<210> SEQ ID NO 8
<211> LENGTH: 29
<212> TYPE: DNA
<213> ORGANISM: Artificial Sequence
<220> FEATURE:
<223> OTHER INFORMATION: Synthetic primer FLAG-(G)

<400> SEQUENCE: 8

atggactata aagatgacga tgacaaagg                                       29


<210> SEQ ID NO 9
<211> LENGTH: 30
<212> TYPE: DNA
<213> ORGANISM: Artificial Sequence
<220> FEATURE:
<223> OTHER INFORMATION: Synthetic primer Dab_216-97_335R

<400> SEQUENCE: 9

gacactaatg cctgataccc actctagacc                                      30
```

COMPOSITION FOR SYNTHESIZING PROTEIN WITH REDUCED LIPOPOLYSACCHARIDE CONTAMINATION, METHOD FOR PRODUCING PROTEIN USING SAID COMPOSITION

CROSS-REFERENCES TO RELATED APPLICATIONS

This application is based on patent application No. 2011-53547 filed in Japan (filing date: Mar. 10, 2011), the contents of which are incorporated in full herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: one 2,359 bytes ASCII (Text) file named "708098SequenceListing.txt," created Sep. 21, 2011

TECHNICAL FIELD

The present invention relates to a composition for synthesizing a protein with reduced lipopolysaccharide contamination, a method for producing a protein using the composition and the like.

BACKGROUND ART

In recent years, an enormous amount of genetic information has been compiled by genomic analyses of various organisms including humans. These pieces of information represent vast gene libraries that have been created by life. In post-genome researches, there is a strong demand for establishing a technique used to select genetic information for a protein (polypeptide) having the desired function with rapidity and high accuracy. One of the methodologies therefor is the display technology. The display technology refers to a technology by which a gene library is screened to select a nucleic acid that encodes a polypeptide having a particular function, such as the specific binding to a target substance, while a polypeptide responsible for a function has a one to one correspondence with a nucleic acid that encodes said polypeptide.

Ribosome display technology has been developed as a method for bringing the display technology into practical use (patent documents 1-8, non-patent document 1). Ribosome display is a technology used to present a polypeptide in the form of a tripartite complex consisting of mRNA-ribosome-polypeptide formed during translation reaction. By forming the tripartite complex, the correspondence of gene product to genetic information is realized. A target substance and the above-described tripartite complex are contacted with each other, a tripartite complex comprising the desired polypeptide is selected by utilizing the specific binding of the polypeptide to the target substance, and the mRNA contained in this tripartite complex is amplified, whereby the nucleic acid that encodes the desired polypeptide can be acquired. Therefore, to suppress the non-specific binding of the tripartite complex to the target substance and the carrier for binding the same is important in acquiring the nucleic acid that encodes the desired polypeptide with high accuracy and high efficiency.

A cell-free protein synthesis system is normally utilized to form the above-described tripartite complex in ribosome display. The cell-free protein synthesis system is a methodology used to synthesize a protein in vitro by utilizing the factors necessary for protein synthesis contained in cell-extracts such as of *Escherichia coli*, wheat germ, rabbit reticulocytes, or cultured cells (non-patent document 2). The cell-free protein synthesis system allows the desired protein to be synthesized merely by adding gene (DNA or RNA) for said protein to the reaction system and incubating the system, representing the most convenient among the various methods for acquiring the desired protein. Above all, the method using *Escherichia coli* extract is most commonly utilized for the reasons of large amounts of protein synthesized and the like. However, cell-extracts also contain a large number of contaminating ingredients that are irrelevant to protein synthesis reaction, posing problems such as the degradation of RNA and protein and the overconsumption of energy (non-patent documents 3 and 4).

A reconstituted cell-free protein synthesis system that has recently been developed by a group including the present inventor is a synthesis system consisting exclusively of specified factors involved in protein synthesis reaction, such as translation factors and ribosome (patent document 9, non-patent document 5). Because the reconstituted cell-free protein synthesis system is a synthesis system prepared by reconstituting independently purified factors, degradation of RNA and enzyme reactions that are irrelevant to protein synthesis reaction, such as metabolic reactions, observed with the use of cell-extracts, are hardly detected. Furthermore, because the composition of the synthesis reaction mixture can be easily adjusted, the reconstituted cell-free protein synthesis system is the cell-free protein synthesis system best-suited for ribosome display (patent documents 10 and 11, non-patent document 6).

PRIOR ART DOCUMENTS

Patent Documents

[patent document 1]U.S. Pat. No. 5,658,754
[patent document 2]U.S. Pat. No. 5,643,768
[patent document 3]JP-B-3127158
[patent document 4]WO01/75097
[patent document 5]U.S. Pat. No. 6,348,315
[patent document 6]JP-T-2001-521395
[patent document 7]U.S. Pat. No. 6,620,587
[patent document 8]JP-T-2002-500514
[patent document 9]JP-B-4061043
[patent document 10]JP-A-2008-271903
[patent document 11]JP-A-2009-112286

Non-Patent Documents

[non-patent document 1]L. C. Mattheakis et al., Proc. Natl. Acad. Sci. USA (1994) vol. 91, p. 9022-9026
[non-patent document 2]L. Jermutus et al., (1998) Curr. Opin. Biotechnol., vol. 9, p. 534-548
[non-patent document 3]D. A. Steege, (2000) RNA, vol. 6, p. 1079-1090
[non-patent document 4]S. V. Matveev, at al., (1996) Biochim. Biophys. Acta, vol. 1293, p. 207-212
[non-patent document 5]Y. Shimizu at al., (2001) Nat. Biotechnol., vol. 19, p. 751-755
[non-patent document 6]E. Osada at al., (2009) J. Biochem., vol. 145, p. 693-700

SUMMARY OF THE INVENTION

It is an object of the present invention to provide a means capable of acquiring a nucleic acid that encodes the desired polypeptide in ribosome display more efficiently.

To solve the above-described problems, the present inventors conducted extensive investigations of a method capable of suppressing the non-specific binding of an mRNA-ribosome-polypeptide tripartite complex to a solid phase carrier for immobilizing the target substance. As a result, unexpectedly, it was found that the non-specific binding of the tripartite complex to a protein that works as a blocking agent to the solid phase carrier is facilitated by contaminating lipopolysaccharide (LPS) in the system. Then, the present inventors found that the lipopolysaccharide was derived from the cell-free protein synthesis system, and that by removing the lipopolysaccharide from the cell-free protein synthesis system, it is possible to suppress the above-described non-specific binding and select a nucleic acid that encodes the desired polypeptide with higher efficiency. The present inventors conducted further investigations based on these findings, and have developed the present invention.

Accordingly, the present invention relates to the following:

[1] A composition possessing cell-free protein synthesis activity and comprising independently purified factors, wherein the lipopolysaccharide content is $1.0\times10^4$ EU/ml or less.

[2] The composition described in [1], wherein the lipopolysaccharide content is $1.0\times10^3$ EU/ml or less.

[3] The composition described in [1], wherein the lipopolysaccharide content is $1.0\times10^2$ EU/ml or less.

[4] The composition described in [1], wherein the independently purified factors comprise at least an initiation factor, an elongation factor, an aminoacyl-tRNA synthetase, a ribosome, an amino acid, a nucleoside triphosphate and a tRNA.

[5] The composition described in any one of [1] to [4], wherein the independently purified factors comprise a ribosome having a lipopolysaccharide content of 7 EU or less per pmol of ribosome.

[6] The composition described in [5], wherein the ribosome is a ribosome with a reduced lipopolysaccharide content, obtained by a washing step using a buffer solution comprising a surfactant.

[7] The composition described in [5], wherein the ribosome is a ribosome with a reduced lipopolysaccharide content, obtained by a method comprising the following steps:(I) mixing a surfactant and a ribosome contaminated with lipopolysaccharide, (II) warming the obtained mixture to a temperature not lower than the clouding point of the surfactant, (III) centrifuging the warmed mixture to achieve phase separation, and (IV) isolating the phase containing the ribosome to obtain a ribosome with a reduced lipopolysaccharide content.

[8] The composition described in [6] or [7], wherein the surfactant comprises one or two or more surfactants selected from the group consisting of polyoxyethylene sorbitan alkyl ethers (Tweens), polyoxyethylene alkyl ethers (Brijs), polyoxyethylene octylphenyl ethers (Triton Xs), alkylglucosides, N-gluco-N-methyl alkanamides, bile salts, amine oxides, and alkyl-N,N-dimethylammoniopropane sulfonates.

[9] The composition described in any one of [1] to [8], wherein the independently purified factors comprise a tRNA having a lipopolysaccharide content of 100 EU or less per Abs unit.

[10] The composition described in any one of [1] to [9], wherein the independently purified factors further comprise methionyl-tRNA transformylase and 10-formyl 5,6,7,8-tetrahydrofolate.

[11] The composition described in any one of [1] to [10], wherein the independently purified factors further comprise a release factor.

[12] The composition described in any one of [1] to [11], wherein the composition does not comprise any release factors.

[13] The composition described in any one of [1] to [12], wherein at least one of the independently purified factors is a factor extracted from a prokaryote.

[14] The composition described in [13], wherein the prokaryote is *Escherichia coli*.

[15] The composition described in any one of [1] to [14], consisting of the independently purified factors.

[16] The composition described in any one of [1] to [15], which is for use in cell-free protein synthesis.

[17] The composition described in any one of [1] to [15], which is for use in ribosome display.

[18] A method for producing a polypeptide, comprising translating an mRNA into a polypeptide in the composition described in any one of [1] to [17].

[19] A method for isolating a nucleic acid that encodes a polypeptide that binds to a target substance, comprising the following steps:

(a) a step for translating an mRNA into a polypeptide in the composition described in any one of [1] to [17] to form a complex comprising the mRNA and the polypeptide, (b) a step for contacting the complex formed in (a) with the target substance, and (c) a step for recovering the complex bound to the target substance, and isolating the mRNA that constitutes the recovered complex or a cDNA thereof as a nucleic acid that encodes a polypeptide that binds to the target substance.

[20] The method described in [19], wherein the complex comprising the mRNA and the polypeptide is formed by a step for translating the mRNA into the polypeptide in the composition described in [12], and wherein the mRNA comprises a stop codon on the 3'-terminus of the polypeptide-coding sequence.

[21] The method described in [19] or [20], wherein the target substance is bound to a solid phase or labeled with a binding partner to be captured by a solid phase.

[22] A kit for isolating a nucleic acid that encodes a polypeptide that binds to a target substance, comprising the following constituents:

(1) the composition described in any one of [1] to [17], and (2) a solid phase carrier for immobilizing the target substance.

[23] A method for producing a ribosome with a lipopolysaccharide content reduced to 7 EU or less per pmol of ribosome, comprising a step of washing the ribosome with a surfactant.

[24] A method for producing a ribosome with a lipopolysaccharide content of 7 EU or less per pmol of the ribosome, comprising repeating the following steps until the lipopolysaccharide content becomes 7 EU or less per pmol of the ribosome:

(I) mixing a surfactant and a ribosome contaminated with lipopolysaccharide, (II) warming the obtained mixture to a temperature not lower than the clouding point of the surfactant, (III) centrifuging the warmed mixture to achieve phase separation, and (IV) isolating the phase containing the ribosome to obtain a ribosome with a reduced lipopolysaccharide content.

[25] The method described in [23] or [24], wherein the surfactant comprises one or two or more surfactants selected from the group consisting of polyoxyethylene sorbitan alkyl ethers, polyoxyethylene alkyl ethers, polyoxyethylene octylphenyl ethers, alkylglucosides, N-gluco-N-methyl alkanamides, bile salts, amine oxides, and alkyl-N,N-dimethylammoniopropane sulfonates.

Effect of the Invention

According to the present invention, a composition possessing protein synthesis activity with reduced contamination of lipopolysaccharide, and a method for producing a protein using the same are provided. When ribosome display is performed using the composition and the method for protein production of the present invention, the background due to the non-specific binding is reduced, so that a nucleic acid that encodes the desired polypeptide can be selected with high accuracy and high efficiency.

MODES FOR CARRYING OUT THE INVENTION

Figure 1:
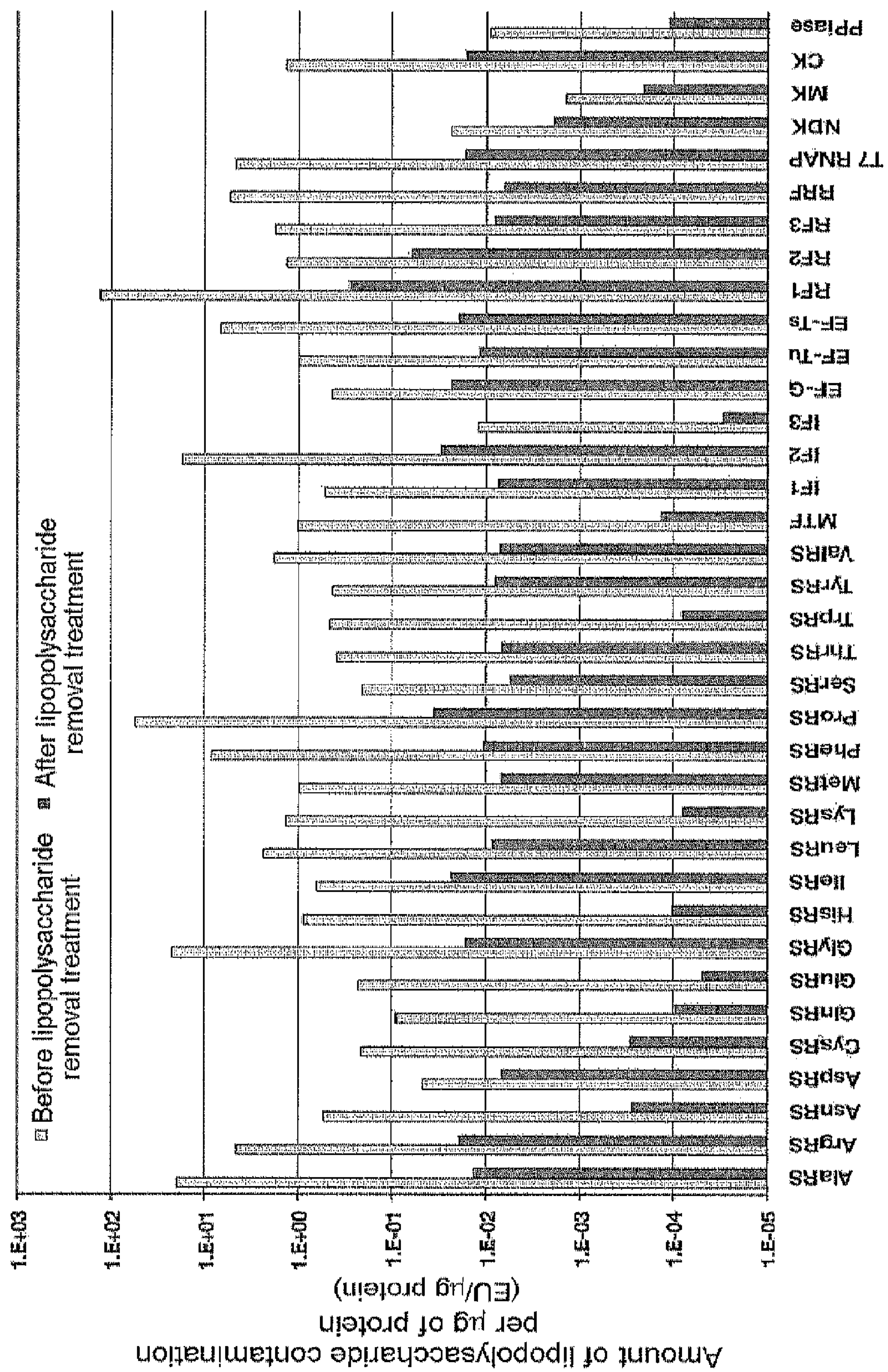
FIG. 1 shows the amounts of contaminating lipopolysaccharide in the proteinous factor. Shown are the amounts of contaminating lipopolysaccharide in 36 kinds of protein factors to be added to a reconstituted cell-free protein synthesis system, before and after removal treatment of lipopolysaccharide.

The present invention provides a composition possessing a protein synthesis activity and comprising independently purified factors, wherein the lipopolysaccharide content is $1.0\times10^4$ EU/ml or less.

Herein, "cell-free protein synthesis" refers to a protein synthesis using a reaction mixture comprising factors necessary for protein synthesis without the need for living cells, and is also referred to as in vitro translation. That is, cell-free protein synthesis is characterized in that the living cells are not required in translating an mRNA into a polypeptide. The cell-free protein synthesis in the present invention comprises a system for performing translation or both transcription and translation. Hence, the cell-free protein synthesis of the present invention comprises either one of the following:

(1) translating an mRNA into a polypeptide; or (2) transcribing a DNA into an mRNA, and translating the mRNA into a polypeptide.

Herein, "protein synthesis activity" means an activity to (1) translate an mRNA into a polypeptide, or (2) transcribe a DNA into an mRNA, and translate the mRNA into a polypeptide, when the mRNA or the DNA that encodes the polypeptide is added to the reaction mixture. "Cell-free protein synthesis activity" means that living cells are not required for the above-described activity.

Herein, a composition possessing cell-free protein synthesis activity is referred to as a "cell-free protein synthesis system".

In the present invention, a polypeptide refers to a conjugate in which two or more amino acids bind together via peptide bonds, and includes peptides, oligopeptides and the like. A protein refers to the same entity.

The content of lipopolysaccharide contained in the composition of the present invention is $1.0\times10^4$ EU/ml or less. Lipopolysaccharide is a constituent component of the outer membrane of Gram-negative bacteria such as *Escherichia coli*, assuming a structure comprising a glycolipid called lipid A and a sugar chain consisting of a large number of sugars bound thereto. Because lipopolysaccharide is released into a homogenate under ordinary conditions for homogenization of *Escherichia coli* cells, lipopolysaccharide is often present as a contaminant in protein fractions and the like isolated from *Escherichia coli*. The present inventors found that the non-specific binding of a tripartite complex consisting of mRNA-ribosome-polypeptide to a carrier for immobilizing the target substance is facilitated by the contaminating lipopolysaccharide in the reaction mixture of ribosome display using a cell-free protein synthesis system, and that the lipopolysaccharide is derived from the cell-free protein synthesis system. Therefore, it is possible to suppress the non-specific binding of the tripartite complex consisting of mRNA-ribosome-polypeptide to the carrier for immobilizing the target substance, and select a nucleic acid that encodes the desired polypeptide with higher efficiency by performing ribosome display using the composition of the present invention with a reduced content of lipopolysaccharide. From this viewpoint, it is preferable that the content of lipopolysaccharide contained in the composition of the present invention be as low as possible. The content of lipopolysaccharide contained in the composition of the present invention is preferably $1.0\times10^3$ EU/ml or less, more preferably $1.0\times10^2$ EU/ml or less. The content of lipopolysaccharide can be measured using a commercially available endotoxin assay kit, and is herein shown as values obtained using the Limulus Color KY Test Wako (Wako Pure Chemical).

The composition of the present invention is a reconstituted cell-free protein synthesis system comprising independently purified factors. Preferably, the composition of the present invention consists of independently purified factors. This reconstituted cell-free protein synthesis system is capable of remarkably suppressing the contamination by ingredients that make the tripartite complex unstable, such as nucleases and proteases, compared with a cell-free protein synthesis system using cell-extracts. For this reason, when ribosome display is performed by the method described below using the composition of the present invention, it is possible to stably maintain the complex, which comprises the mRNA and the polypeptide, and finally the nucleic acid that encodes the desired polypeptide is efficiently isolated. Also, it is possible to reduce the amount of contaminating lipopolysaccharide contained in the entire composition of the present invention by removing the lipopolysaccharide that contaminates each factor fraction at the stage of independently purifying each factor. For this reason, when ribosome display is performed using the composition of the present invention, it is possible to suppress the non-specific binding of the tripartite complex to any protein that works as a blocking reagent on the solid phase carrier for immobilizing the target substance, and acquire the nucleic acid that encodes the desired polypeptide with high accuracy and high efficiency.

Herein, "factors" refer to constituent units of a cell-free protein synthesis system that can be purified independently. The factors include a protein that works as monomer and a low-molecular weight compound of a substrate, a salt and the like. Furthermore, various complexes and mixtures that can be isolated from a crude fraction are also included. For example, factors to be purified as a complex include dimer proteins, ribosomes and the like. Mixtures include tRNA mixtures and the like. "Independently purified factors" refer to factors that have been purified from other factors by respective independent process. It is possible to construct a cell-free protein synthesis system by mixing and reconstituting as required the independently purified factors necessary for protein synthesis. Factors that present in a mixed fraction containing a plurality of kinds of factors without being isolated from the cell extract are not said to be independently purified factors. Meanwhile, even in the case of a complex consisting of a plurality of components, the complex is "independently purified factors" in the present invention, provided that it has been purified as single factors. For example, a purified ribosome is a complex consisting of some elements, and it is an "independently purified factor" because it can be purified as a single factor.

Herein, a "purified state" means that a process has been performed to remove substances other than the desired factor from the fraction containing the desired factor to the maximum possible extent. When the factor consists of a protein, the purity of the desired factor in the "purified factor" (ratio by weight of the desired factor to the total protein weight) is, for example, 20% or more, preferably 50% or more, more preferably 70% or more, still more preferably 90% or more, most preferably 99% or more (for example, 100%). When the factor consists of a nucleic acid, the purity of the desired factor in the "purified factor" (ratio by weight of the desired factor to the total nucleic acid weight) is, for example, 20% or more, preferably 50% or more, more preferably 70% or more, still more preferably 90% or more, most preferably 99% or more (for example, 100%). When the factor is a complex consisting of a protein and a nucleic acid (for example, when the factor is a ribosome), the purity of the desired factor in the "purified factor" (ratio by weight of the desired factor to the total protein and nucleic acid weight) is, for example, 20% or more, preferably 50% or more, more preferably 70% or more, still more preferably 90% or more, still yet more preferably 99% or more (for example, 100%).

Independently purified factors can be obtained by synthesizing them by a chemical synthesis, enzymatic reaction, or combination thereof, and then purifying them.

Independently purified factors can also be obtained by purifying from extracts of a wide variety of cells. Cells for purifying the factors include, for example, prokaryotic cells and eukaryotic cells. Prokaryotic cells include *Escherichia coli* cells, extreme-thermophilic bacterial cells, and *Bacillus subtilis* cells. The prokaryotic cell is preferably *Escherichia coli* cell. Eukaryotic cells include yeast cells, plant cells, insect cells, and mammalian cells. In particular, when the independently purified factors consist of a protein only, each factor can be obtained by one of the methods shown below.

(1) Isolating a gene that encodes each factor (protein) and introducing into an expression vector, after which an appropriate host cell is transformed therewith to express the factor, and the desired factor is extracted from the transformant.

(2) Isolating a gene that encodes each factor, synthesizing the factor using a cell-free protein synthesis system, and recovering it.

In (1), first, an expression plasmid is prepared by integrating the gene for each factor into an expression vector comprising an expression regulatory region so that the desired factor will be expressed by control of the region. An expression regulatory region that constitutes the vector refers to, for example, an enhancer, a promoter, a terminator and the like. The expression vector can comprise a drug resistance marker and the like. Next, host cells are transformed with this expression plasmid to allow each factor to be expressed.

When using, for example, *Escherichia coli* such as JM109, DH5α, HB101, XL1-Blue, or BL21(DE3) as host cells, the lacZ promoter (Ward et al., Nature (1989) vol. 341, p. 544-546, FASEB J. (1992) vol. 6, p. 2422-2427), the araB promoter (Better et al., Science (1988) vol. 240, p. 1041-1043), the T7 promoter and the like can be mentioned as examples. Expression vectors having such a promoter are exemplified by pGEX (manufactured by GE Healthcare Biosciences), pQE (manufactured by Qiagen), and pET (manufactured by Novagen). An expression plasmid into which the gene encoding each factor is incorporated can be introduced into *Escherichia coli* by, for example, the calcium chloride method or the electroporation method.

The expressed (synthesized) desired factor can easily be purified by labeling the same with either one of mutually adhering substances. For example, the factor is labeled with a histidine tag, which adheres to a metal affinity resin column retaining the nickel ion or the like, glutathione S-transferase, which adheres to a glutathione-Sepharose resin column, or an epitope tag, which adheres to an affinity resin column, such as an antibody-immobilized resin column. This labeling can be achieved by, for example, integrating a gene that encodes the desired factor into an expression vector containing a nucleic acid sequence that encodes such a label to allow a fusion protein thereof to be expressed. A protease recognition sequence may be inserted between the two. It is possible to capture the fusion protein using a solid phase carrier that binds to the label, allow a protease that cleaves the recognition sequence to act, and recover the desired factor. Methods of thus purifying a factor are publicly known (K. Boon et al., Eur. J. Biochem. (1992) vol. 210, p. 177-183, K. S. Wilson et al., Cell (1998) vol. 92, p. 131-139, Yu-Wen Hwang et al., Arch. Biochem. Biophy. (1997) vol. 348, p. 157-162).

In a preferred mode of embodiment, the composition of the present invention comprises, for example, at least the following factor in an independently purified state:

an initiation factor (IF),
an elongation factor (EF),
an aminoacyl-tRNA synthetase (AARS),
a ribosome,
an amino acid,
a nucleoside triphosphate, and
a tRNA.

These factors are not limited to those derived from prokaryotic cells such as *Escherichia coli*; those derived from eukaryotic cells can also be used.

The initiation factor used in the composition of the present invention is a factor that is essential for the formation of translation initiation complex or remarkably promotes the formation; those derived from *Escherichia coli* are known as IF1, IF2 and IF3 (Claudio O et al. (1990) Biochemistry, vol. 29, p. 5881-5889). The initiation factor IF3 promotes the dissociation of the 70S ribosome into the 30S subunit and the 50S subunit, which is necessary for the initiation of translation, and inhibits the insertion of any tRNAs other than formylmethionyl-tRNA to the P-site during the formation of the translation initiation complex. The initiation factor IF2 binds to formylmethionyl-tRNA and transports the formylmethionyl-tRNA to the P-site of the 30S ribosome subunit to form translation initiation complex. The initiation factor IF1 promotes the functions of the initiation factors IF2 and IF3. Examples of preferred initiation factors for use in the present invention include those derived from *Escherichia coli*, for example, those derived from the *Escherichia coli* K12 strain, but those derived from eukaryotic cells can also be used. When using an *Escherichia coli*-derived initiation factor, the same can be used at, for example, 0.005 μM-300 μM, preferably at 0.02 μM-100 μM. When using all of IF1, IF2, and IF3 as initiation factors, the amount of each factor used can be selected within the range shown above for exemplification.

The elongation factor used in the composition of the present invention includes those derived from *Escherichia coli* known as EF-Tu, EF-Ts and EF-G. The elongation factor EF-Tu occurs in two forms: GTP-form and GDP-form; the GTP-form binds to aminoacyl-tRNA and transports the same to the A-site of the ribosome. As EF-Tu leaves the ribosome, GTP is hydrolyzed and GTP-form turns into the GDP-form (Pape T et al, (1998) EMBO J, vol. 17, p. 7490-7497). The elongation factor EF-Ts binds to EF-Tu (GDP-form) to promote the conversion to the GTP-form (Hwang Y W et al. (1997) Arch. Biochem. Biophys. vol. 348, p. 157-162). The elongation factor EF-G promotes the translocation reaction following the peptide bond formation reaction in the peptide chain elongation process (Agrawal R K et al, (1999) Nat. Struct. Biol., vol. 6, p. 643-647, Rodnina M W. et al, (1999) FEMS Microbiology Reviews, vol. 23, p. 317-333). Examples of preferred elongation factors for use in the present invention include those derived from *Escherichia coli*, for example, those derived from the *Escherichia coli* K12 strain, but those derived from eukaryotic cells can also be used. When using an *Escherichia coli*-derived elongation factor, the same can be used at, for example, 0.005 μM-300 μM, preferably at 0.02 μM-100 μM. When using all of EF-Tu, EF-Ts, and EF-G as elongation factors, the amount of each factor used can be selected within the range shown above for example.

An aminoacyl-tRNA synthetase is an enzyme that allows an amino acid to attach to a tRNA covalently in the presence of ATP to synthesize an aminoacyl-tRNA. Aminoacyl-tRNA synthetases corresponding to each amino acid exist (Francklyn C et al, (1997) RNA, vol. 3, p. 954-960; Protein, Nucleic Acid, and Enzyme, vol. 39, p. 1215-1225 (1994)). Examples of preferred aminoacyl-tRNA synthetases for use in the present invention include those derived from *Escherichia coli*, for example, those derived from the *Escherichia coli* K12 strain, but those derived from eukaryotic cells can also be used. An artificial aminoacyl-tRNA synthetase that recognizes a non-natural amino acid (Japanese Patent 2668701 and the like) can also be used. When using an *Escherichia coli*-derived aminoacyl-tRNA synthetase, the same can be used at, for example, 1 U/ml-1,000,000 U/ml, preferably at 5 U/ml-500,000 U/ml. Alternatively, the same can be used at 0.001 μg/ml-10,000 μg/ml, preferably at 0.01 μg/ml-1,000 μg/ml. The amounts of aminoacyl-tRNA synthetase used shown here for exemplification are applicable to all aminoacyl-tRNA synthetases corresponding to each amino acid. Here, the activity for forming 1 pmol of the aminoacyl-tRNA in 1 minute is defined as 1 U.

The ribosome is a huge complex composed of a several kinds of ribosomal RNAs and several tens of kinds of ribosomal proteins. In the cell, the ribosome functions as the place for protein synthesis reaction. Basically, the ribosome consists of two subunits, large and small; the constitution of the components and the size of the ribosome differ between prokaryotes and eukaryotes. The ribosome and the subunits that constitute the same can be separated from each other by sucrose density gradient centrifugation and the like, the sizes thereof being expressed by sedimentation coefficient. Specifically, in prokaryotes, the ribosome and the subunits that constitute the same have the following sizes, respectively:

| Ribosome (70S) = Molecular weight: | large subunit (50S) + | small subunit (30S) |
|---|---|---|
| about $2.5 \times 10^6$ | about $1.6 \times 10^6$ | about $0.9 \times 10^6$. |

Describing in more detail, the SOS subunit and the 30S subunit have been shown to be composed of the components shown below, respectively.

50S Subunit;
- 34 kinds of proteins (ribosome proteins) L1 to L34
- 23S RNA (about 3200 nucleotides)
- 5S RNA (about 120 nucleotides)

30S Subunit;
- 21 kinds of proteins (ribosome proteins) S1 to S21
- 16S RNA (about 1540 nucleotides)

Hence, each subunit can be isolated as a complex consisting of these components. Furthermore, the ribosome can be isolated as a complex of each subunit. Therefore, an independently purified ribosome in the present invention refers to, for example, a complex purified as the 70S ribosome consisting of the large and small subunits, or a complex formed by mixing the separately purified 50S subunit and 30S subunit, for a prokaryote-derived ribosome.

Meanwhile, in eukaryotic cells, the ribosome and the subunits constituting the same have the following sizes, respectively:

Ribosome (80S)=large subunit (60S)+small subunit (40S)

Therefore, when the cell-free protein synthesis system in the present invention is to be constituted with a eukaryotic cell-derived ribosome, a ribosome purified as the 80S ribosome can be utilized.

Ribosome can be purified from cultured *Escherichia coli* by, for example, the method disclosed in JP-A-2008-271903. Because prokaryotes such as *Escherichia coli* can be easily cultivated in large scale, prokaryotes are preferred for preparing a ribosome in large amounts. The ribosome purified by the method disclosed in JP-A-2008-271903 is preferable as an independently purified ribosome in the present invention because it is substantially free from nuclease activity. As stated above, to achieve efficient polypeptide synthesis and polypeptide screening by ribosome display, it is desirable to use a cell-free protein synthesis system that is substantially free from nuclease activity. For this reason, a ribosome that is substantially free from nuclease activity is suitably used in the present invention. When using an *Escherichia coli*-derived ribosome in the composition of the present invention, the same can be used at concentrations of, for example, 0.01 μM-50 μM, preferably 0.05 μM-10 μM.

Regarding each factor used in the composition of the present invention, "being derived from an organism X" means that the amino acid sequence or nucleic acid sequence of the factor has substantially the same amino acid sequence or nucleic acid sequence as the amino acid sequence or nucleic acid sequence of the factor expressing naturally in the organism X. "Substantially the same" means that the amino acid sequence or nucleic acid sequence of interest has an identity of 70% or more (preferably 80% or more, more preferably 90% or more, still more preferably 95% or more, most preferably 99% or more) to the amino acid sequence or nucleic acid sequence of the factor expressing naturally in the organism X, and that the function of the factor is maintained.

A useful amino acid includes a non-natural amino acid as well as a natural amino acid. These amino acids are attached to tRNA by the action of an aminoacyl-tRNA synthetase that constitutes the cell-free protein synthesis system. Alternatively, the amino acid may be previously charged to tRNA and added to the cell-free protein synthesis system. In the present invention, charging an amino acid to a tRNA refers to allowing an amino acid to bind to a tRNA to render the amino acid in a state utilizable for the translation reaction in the ribosome. By adding a non-natural amino acid in the presence of an artificial aminoacyl synthetase that recognizes the non-natural amino acid, or using a tRNA charged with a non-natural amino acid, it is possible to introduce a non-natural amino acid at a specific codon of a protein. When using a natural amino acid, the same can be used at, for example, 0.001 mM-20 mM, preferably at 0.01 mM-5 mM.

A useful tRNA includes a tRNA purified from cells of prokaryotes such as *Escherichia coli* and eukaryotes such as yeast. A tRNA prepared from a DNA that encodes the tRNA by transcription reaction using RNA polymerase can also be used. An artificial tRNA with directed mutation at anticodon or another base can also be used (Hohsaka, T et al. (1996) J. Chem. Soc., vol. 121, p. 34-40, Hirao T et al (2002) Nat. Biotechnol., vol. 20, p. 177-182). For example, by charging a tRNA having CUA as anticodon with a non-natural amino acid, it is possible to translate the UAG codon, which is normally a stop codon, into the non-natural amino acid. Also, by using an artificial aminoacyl-tRNA prepared by charging a tRNA having a 4-base codon as anticodon with a non-natural amino acid, it is possible to translate 4-base codon that does not exist naturally into the non-natural amino acid (Hohsaka et al. (1999) J. Am. Chem. Soc., vol. 121, p. 12194-12195). To prepare such an artificial aminoacyl-tRNA, a method using RNA can also be used (JP-T-2003-514572). These methods allow a protein having a site-specifically introduced non-natural amino acid to be synthesized. When using tRNA mixture derived from *Escherichia coli*, the tRNA can be used at, for example, 0.1 $A_{260}$/ml-1000 $A_{260}$/ml, preferably at 1 $A_{260}$/ml-300 $A_{260}$/ml.

Nucleoside triphosphates (ATP, GTP, CTP, UTP and the like) are substrates and/or energy sources for transcription and/or translation reactions. Nucleoside triphosphates can be used normally at 0.01 mM-500 mM, preferably at 0.1 mM-50 mM. When the cell-free protein synthesis system consists of a translation reaction only, the system may comprise ATP and GTP only.

By adding the factors that constitute the above-described cell-free protein synthesis system to a buffered aqueous solution that maintains a pH suitable for the transcription and translation, the composition of the present invention can be obtained. Suitable pH is, for example, pH 6 to pH 9, preferably pH 7 to 8. Buffer solutions used in the present invention include potassium phosphate buffered aqueous solutions (pH 7.3), Hepes-KOH (pH 7.6) and the like. When using Hepes-KOH (pH 7.6), the same can be used at, for example, 0.01 mM-200 mM, preferably at 0.1 mM-100 mM.

A salt can be added to the composition of the present invention for the purpose of protecting factors and maintaining the activity thereof. Specifically, potassium glutamate, potassium acetate, ammonium chloride, magnesium acetate, magnesium chloride, calcium chloride and the like can be mentioned. These salts are used normally at 0.01 mM-1000 mM, preferably at 0.1 mM-300 mM.

Other low-molecular weight compounds can be added to the composition of the present invention as an enzyme substrate and/or for the purpose of improving and maintaining the activity of each factor. Specifically, polyamines such as putrescine and spermidine, reducing agents such as dithiothreitol (DTT) and the like can be added to the composition of the present invention. These low-molecular weight compounds can be used normally at 0.01 mM-1000 mM, preferably at 0.1 mM-200 mM.

In the case of a reaction system using a factor derived from prokaryotic cells such as of *Escherichia coli*, it is preferable that the composition of the present invention further comprises methionyl-tRNA transformylase and 10-formyl 5,6,7,8-tetrahydrofolate (FD).

Methionyl-tRNA transformylase (MTF) is an enzyme for synthesizing the N-formylmethionyl-(fMet-)initiator tRNA, wherein a formyl group is attached to the amino group of methionine covalently bound to the initiator tRNA in protein synthesis in a prokaryote. Hence, methionyl-tRNA transformylase allows the formyl group of FD to transfer to the amino group of the methionyl-initiator tRNA corresponding to the initiation codon to convert the same to the fMet-initiator tRNA (Ramesh V et al, (1999) Proc. Natl. Acad. Sci. USA, vol. 96, p. 875-880). The added formyl group is recognized by the initiation factor IF2 and acts as a protein synthesis initiation signal. In eukaryote, although MTF is not present in the protein synthesis system in the cytoplasm, the same is present in the mitochondria and chloroplasts. Examples of preferred MTFs for use in the present invention include those derived from *Escherichia coli*, for example, those derived from the *Escherichia coli* K12 strain. When using an MTF derived from *Escherichia coli*, the same can be used at, for example, 100 U/ml-1,000,000 U/ml, preferably at 500 U/ml-400,000

U/ml. Here, the activity for forming 1 pmol of the fMet-initiation tRNA in 1 minute is defined as 1 U. Alternatively, the same can be used at 0.01 μg/ml-10,000 μg/ml, preferably at 0.05 μg/ml-1,000 μg/ml. The formyl donor (FD), which is the substrate for MTF, can be used at, for example, 0.1 μg/ml-1000 μg/ml, preferably at 1 μg/ml-100 μg/ml.

In a mode of embodiment, the composition of the present invention comprises a release factor (RF) and/or ribosome recycling factor (RRF). A release factor is essential to the completion of protein synthesis reaction and the release of the translated peptide chain. Ribosome recycling factor is essential to the regeneration recycling of the ribosome for the initiation of the translation from the next mRNA. Therefore, by carrying out a cell-free protein synthesis reaction using the composition of the present invention comprising a release factor and/or ribosome recycling factor, a larger amount of polypeptide can be produced. The release factor used in the composition of the present invention includes those derived from *Escherichia coli* known as RF1, RF2 and RF3. The release factors RF1 and RF2 enter the A-site to promote the release of the peptide chain from peptidyl-tRNA (present at the P-site) upon reach of the A-site of the ribosome to the stop codon (UAA, UAG, UGA) on the mRNA. RF1 recognizes UAA and UAG as stop codons, whereas RF2 recognizes UAA and UGA. The release factor RF3 promotes the release of RF1 and RF2 from the ribosome after the release reaction of the peptide chain by RF1 and RF2. Ribosome recycling factor promotes the release of the tRNA remaining at the P-site after the release of the synthesized peptide chain and the recycling of the ribosome for the next protein synthesis. The functions of the release factors RF1, RF2, RF3 and RRF are described in Freistroffer D V et al, (1997) in EMBO J., vol. 16, p. 4126-4133, and Pavlov M Y et al. (1997) EMBO J., vol. 16, p. 4134-4141. Examples of preferred release factors for use in the present invention include those derived from *Escherichia coli*, for example, those derived from the *Escherichia coli* K12, but those derived from eukaryotic cells can also be used. Examples of preferred ribosome recycling factors for use in the present invention include those derived from *Escherichia coli*, for example, those derived from the *Escherichia coli* K12 strain. When using an *Escherichia coli*-derived release factor and/or ribosome recycling factor, the same can be used at, for example, 0.005 μM-200 μM, preferably at 0.02 μM-50 μM. When using all of RF1, RF2, RF3, and RRF, the amount of each factor used can be selected within the range shown above for exemplification.

In a mode of embodiment, the composition of the present invention does not comprise a release factor and/or ribosome recycling factor. Without a release factor and/or ribosome recycling factor, the release of the translated peptide chain and the regeneration of the ribosome for the initiation of the translation from the next mRNA do not occur, so that a tripartite complex consisting of mRNA-ribosome-polypeptide can be stably formed. Therefore, by performing ribosome display using the composition of the present invention not comprising a release factor and/or ribosome recycling factor, a nucleic acid that encodes a polypeptide that binds to the target substance can be isolated with high efficiency.

When using the composition of the present invention to transcribe a DNA to an mRNA and translate the mRNA into a polypeptide, an RNA polymerase for transcription to the mRNA can be contained. Specifically, the RNA polymerases shown below can be utilized in the present invention. These RNA polymerases are commercially available.

T7 RNA polymerase
T3 RNA polymerase
SP6 RNA polymerase

When using T7 RNA polymerase, the same can be used at, for example, 0.01 μg/ml-5000 μg/ml, preferably at 0.1 μg/ml-1000 μg/ml.

The composition of the present invention can comprise, in addition to factors for transcription and translation, an additional factor. Additional factors include, for example, the factors shown below.

Enzymes for regenerating energy in the reaction system:
creatine kinase,
myokinase, and
nucleoside diphosphate kinase and the like;
substrates for enzymes for regenerating energy in the reaction system:
creatine phosphate and the like;
enzymes for degradating inorganic pyrophosphoric acid resulting from transcription/translation:
inorganic pyrophosphatase and the like.

The above-described enzymes can be used at, for example, 0.001 μg/ml-2000 μg/ml, preferably at 0.05 μg/ml-500 μg/ml. The above-described substrates can be used normally at 0.01 mM-1000 mM, preferably at 0.1 mM-200 mM.

Methods for purifying the factors contained in the composition of the present invention are publicly known; ribosome can be purified using the method disclosed in JP-A—2008-271903, and other factors can be purified using the method disclosed in JP-A-2003-102495; it is preferable that lipopolysaccharide be removed to the maximum possible extent in the process for purifying each factor, in order to avoid contamination of lipopolysaccharide in the composition of the present invention to the maximum possible extent. For example, to remove lipopolysaccharide from the protein solution, methods shown in Petsch and Anspach (2000) J. Biotechnol., vol. 76, p. 97-119, Magalhaes et al. (2007) J. Pharm. Pharm. Sci., vol. 10, p. 388-404 and the like can be utilized.

In this case, for all the factors consisting exclusively of proteins, contained in the composition of the present invention, the lipopolysaccharide content is preferably 10 EU or less, more preferably 1 EU or less, still more preferably 0.1 EU or less, per μg of protein. Removal of lipopolysaccharide from the protein solution can be achieved by, for example, binding the desired protein to an affinity column, washing the column with a buffer solution (with the provision that no lipopolysaccharide is contained) containing a surfactant such as Triton X-114 at a concentration that removes lipopolysaccharide (for example, 0.05 to 1(v/v)%), and then eluting the desired protein with an appropriate buffer solution from the column (Reichelt et al., (2006) Protein Expr Purif., vol. 46, p. 483). Any method other than the above-described method can also be used, as far as it allows the amount of contaminating lipopolysaccharide to be preferably 10 EU or less, more preferably 1 EU or less, still more preferably 0.1 EU or less, per μg of protein.

Regarding the tRNA, the amount of contamination is normally 100 EU or less, preferably 10 EU or less, more preferably 1 EU or less, still more preferably 0.1 EU or less, most preferably 0.01 EU or less per Abs unit. Here, 1 Abs unit means the amount of tRNA that gives an absorbance value of 1.0 at 260 nm. Because commercially available tRNA mixtures extracted from a prokaryote such as *Escherichia coli* are contaminated by a large amount of lipopolysaccharide (100 EU or more per Abs unit), it is necessary to remove the lipopolysaccharide before adding them to the composition of the present invention. Removal of lipopolysaccharide from the tRNA mixture can be achieved with reference to a method for removing lipopolysaccharide from a protein solution. For example, a tRNA mixture with a much-reduced amount of contaminating lipopolysaccharide can be obtained by a phase separation method using the surfactant Triton X-114. Specifically, this can be achieved by repeating the process of mixing a buffer solution containing 10(v/v) % Triton X-114 with a tRNA solution in a volume ratio of 1:9 to obtain a homogenous mixture, then warming the mixture to a temperature not lower than the clouding point of Triton X-114 (23° C.), performing phase separation via centrifugation, and recovering the fraction containing the tRNA. Other methods can be used, as far as the amount of contaminating lipopolysaccharide can be made to be normally 100 EU or less, preferably 10 EU or less, more preferably 1 EU or less, still more preferably 0.1 EU or less, most preferably 0.01 EU or less, per Abs unit of tRNA.

The content of contaminating lipopolysaccharide in a ribosome contained in the composition of the present invention is normally 7 EU or less, preferably 1 EU or less, more preferably 0.1 EU or less, per 1 pmol of ribosome. In particular, when using a ribosome extracted from a prokaryote (preferably a Gram-negative bacterium, more preferably *Escherichia coli*) for the composition of the present invention, the ribosome possibly becomes the major cause of contaminating lipopolysaccharide, so that it is preferable to carefully remove the lipopolysaccharide from the ribosome. No method has been reported for removing contaminating lipopolysaccharide from the ribosome, which is a huge complex consisting of several kinds of RNAs and several tens of kinds of proteins with different biochemical characteristics, while maintaining protein synthesis activity. The present inventors investigated a plurality of methods and found that washing with a surfactant is effective.

Surfactants encompass non-ionic surfactants, anionic surfactants, zwitterionic surfactants and the like.

Non-ionic surfactants include polyoxyethylene sorbitan alkyl ethers (Tweens) such as polyoxyethylene sorbitan monolaurate (Tween 20) and polyoxyethylene sorbitan monooleate (Tween 80), polyoxyethylene alkyl ethers (Brijs) such as polyoxyethylene lauryl ether (Brij35) and polyoxyethylene cetyl ether (Brij58), polyoxyethylene octylphenyl ethers (Triton Xs) such as polyoxyethylene (7-8) octylphenyl ether (Triton X-114) and polyoxyethylene (9-10) octylphenyl ether (Triton X-100), alkylglucosides such as n-octyl-β-glucoside, n-dodecyl-β-maltoside, n-octyl-β-thioglucoside, and n-heptyl-β-thioglucoside, N-gluco-N-methyl alkanamides such as N-octanoyl-N-methyl alkanamide (Mega-8), N-nonanoyl-N-methyl alkanamide (Mega-9), and N-decanoyl-N-methyl alkanamide (Mega-10), and the like.

Anionic surfactants include bile salts such as sodium cholate, sodium deoxycholate, sodium taurocholate, and sodium glycocholate, and the like.

Zwitterionic surfactants include amine oxides such as 3-[(3-colamidepropyl)-dimethylammonio]-1-propane sulfonate (CHAPS), 3-[(3-colamidepropyl)-dimethylammonio]-2-hydroxypropane sulfonate (CHAPSO), and N,N-dimethyldodecylamine N-oxide, alkyl-N,N-dimethylammoniopropane sulfonates such as N,N-dimethyldodecylammoniopropane sulfonate, and N,N-dimethylmyristylammoniopropane sulfonate, and the like.

The amount of surfactant added is not particularly limited, as far as contaminating lipopolysaccharide can be removed from the ribosome, and the protein synthesis activity of the ribosome is not lost; the amount can be set as appropriate according to the choice of surfactant, and the amount is normally 0.001 to 10(v/v) %, preferably 0.01 to 5(v/v)%, more preferably 0.05 to 2(v/v)%, as the surfactant concentration in the mixed solution of the surfactant and the ribosome containing contaminating lipopolysaccharide.

In a mode of embodiment, washing of the ribosome with a surfactant can be achieved by dispersing the ribosome in an appropriate buffer solution containing the surfactant to allow the lipopolysaccharide contained in the ribosome to transfer into the buffer solution, and then subjecting this dispersion to sucrose density gradient centrifugation, and recovering a fraction containing the ribosome.

In another mode of embodiment, methods of washing using a surfactant include, for example, the following method using polyoxyethylene (7-8) octylphenyl ether (Triton X-114):

(I) mixing a surfactant and a ribosome containing contaminating lipopolysaccharide, (II) warming the obtained mixture to a temperature not lower than the clouding point of the surfactant, (III) centrifuging the warmed mixture to achieve phase separation, and (IV) isolating the phase containing the ribosome to obtain a ribosome with a reduced lipopolysaccharide content.

Furthermore, the steps (I) to (IV) may be repeated until the lipopolysaccharide content is decreased to not higher than a specified concentration (for example, 7 EU or less, preferably 1 EU or less, more preferably 0.1 EU or less, per pmol of ribosome) by returning the ribosome with a reduced lipopolysaccharide content, obtained in the step (IV), to the step (I).

Specifically, by repeating the process (washing process) of mixing a buffer solution containing 10(v/v) % Triton X-114 with the ribosome in a volume ratio of 1:9 to obtain a homogenous mixture, then warming the mixture to a temperature not lower than the clouding point of Triton X-114 (23° C.), performing phase separation via centrifugation, and separating the fraction containing the ribosome, it is possible to reduce contaminating lipopolysaccharide.

The method for washing the ribosome with a surfactant is not limited to the above-described method; other washing methods can be used, as far as it is possible to reduce the lipopolysaccharide content to not higher than a specified concentration (for example, 7 EU or less, preferably 1 EU or less, more preferably 0.1 EU or less, per pmol of ribosome).

By mixing the ribosome having a reduced lipopolysaccharide content, obtained via the above-described step, with the above-described independently purified factors other than the ribosome (e.g., an initiation factor, an elongation factor, an aminoacyl-tRNA synthetase, an amino acid, a nucleoside triphosphate and a tRNA), the composition of the present invention can be produced. The present invention also provides such a method for producing the above-described composition of the present invention.

In a mode of embodiment, the composition of the present invention comprises a combination of the following independently purified factor:

an initiation factor (IF),
an elongation factor (EF),
an aminoacyl-tRNA synthetase,
a ribosome,
an amino acid,
a nucleoside triphosphate,
tRNA,
methionyl-tRNA transformylase, and
10-formyl 5,6,7,8-tetrahydrofolate.

In a mode of embodiment, the composition of the present invention comprises a combination of the following independently purified factor:

an initiation factor (IF),
an elongation factor (EF),
an aminoacyl-tRNA synthetase, a ribosome,
an amino acid,
a nucleoside triphosphate,
a tRNA,
methionyl-tRNA transformylase,
10-formyl 5,6,7,6-tetrahydrofolate,
a release factor, and
ribosome recycling factor.

A more specific constitution of the composition of the present invention can be prepared on the basis of the description in Shimizu et al. (Shimizu et al., Nat. Biotechnol. (2001) vol. 19, p. 751-755, Shimizu et al., Methods (2005) vol. 36, p. 299-304), or Ying et al. (Ying et al., Biochem. Biophys. Res. Commun. (2004) vol. 320, p. 1359-1364), except that the lipopolysaccharide content is $1.0\times10^4$ EU/ml or less. Specifically, for example, the following content ratio can be mentioned; as stated above, the concentration of each factor can be increased or decreased as appropriate according to the specific activity of the purified factor, the intended use and the like. For example, if the energy consumption becomes large, ATP can be increased. It is also possible to add a particular tRNA according to the frequency of the codon used in the mRNA to be translated.

1.2 μM Ribosome,
2.70 μM IF1,
0.40 μM IF2,
1.50 μM IF3,
0.26 μM EF-G,
0.92 μM EF-Tu,
0.66 μM EF-Ts,
0.25 μM RF1,
0.24 μM RF2,
0.17 μM RF3,
0.50 μM RRF,
1900 U/ml AlaRS,
2500 U/ml ArgRS,
20 μg/ml AsnRS,
2500 U/ml AspRS,
630 U/ml CysRS,
1300 U/ml GlnRS,
1900 U/ml GluRS,
5000 U/ml GlyRS,
630 U/ml HisRS,
2500 U/ml IleRS,
3800 U/ml LeuRS,
3800 U/ml LysRS,
6300 U/ml MetRS,
1300 U/ml PheRS,
1300 U/ml ProRS,
1900 U/ml SerRS,
1300 U/ml ThrRS,
630 U/ml TrpRS,
630 U/ml TyrRS,
3100 U/ml ValRS,
10 μg/ml T7 RNA polymerase,
4500 U/ml Methionyl-tRNA transformylase (MTF),
4.0 μg/ml Creatine kinase,
3.0 μg/ml Myokinase,
1.1 μg/ml Nucleoside-diphosphate kinase,
1.3 μg/ml Pyrophosphatase,
0.3 mM each amino acid,
56 $A_{260}$/ml tRNA,
50 mM Hepes-KOH, pH 7.6,
100 mM Potassium glutamate,
13 mM Magnesium acetate,
2 mM Spermidine,
1 mM DTT,
2 mM ATP,
2 mM GTP,
1 mM CTP,
1 mM UTP,
20 mM Creatine phosphate,
10 μg/ml 10-formyl-5,6,7,8-tetrahydrofolic acid (FD).

In the composition of the present invention, it is preferable that at least one of the independently purified factors be extracted from a prokaryote. In a mode of embodiment, at least one, preferably all, selected from the group consisting of an initiation factor, an elongation factor, an aminoacyl-tRNA synthetase, a ribosome and a tRNA, contained in the composition of the present invention have been extracted from a prokaryote (for example, a Gram-negative bacterium, preferably *Escherichia coli*). In a mode of embodiment, when the composition of the present invention comprises a release factor and ribosome recycling factor, at least one, preferably all, selected from the group consisting of an initiation factor, an elongation factor, an aminoacyl-tRNA synthetase, a ribosome, a release factor, ribosome recycling factor and a tRNA are extracted from a prokaryote (for example, a Gram-negative bacterium, preferably *Escherichia coli*). In a mode of embodiment, the ribosome contained in the composition of the present invention is extracted from a prokaryote (for example, a Gram-negative bacterium, preferably *Escherichia coli*). In a mode of embodiment, the tRNA contained in the composition of the present invention is extracted from a prokaryote (for example, a Gram-negative bacterium, preferably *Escherichia coli*).

The constitution of the composition of the present invention can be adjusted as appropriate according to the polypeptide (protein) to be synthesized (presented), as well as to the above-described basic constitution. For example, in the case of a protein unlikely to form a higher structure, a cell-free protein synthesis system supplemented with a class of proteins called molecular chaperones can be used Specifically, a cell-free protein synthesis system supplemented with Hsp100, Hsp90, Hsp70, Hsp60, Hsp40, Hsp10, small Hsp, a homologue thereof, *Escherichia coli* trigger factor and the like can be mentioned. Molecular chaperones are proteins known to assist protein folding to form a higher-order structure in cells to prevent the protein from aggregating (Bukau and Horwich, Cell (1998) vol. 92, p. 351-366, Young et al., Nat. Rev. Mol. Cell. Biol (2004) vol. 5, p. 781).

In the case of a protein (polypeptide) that forms disulfide bond(s) in the molecule, like antibody molecules, the redox potential of the reaction mixture is important. For this reason, the reducing agent DTT may be removed from the reaction mixture, and a composition supplemented with glutathione may be used. Furthermore, it is possible to use a composition supplemented with an enzyme that promotes the formation of disulfide bond, or isomerizes the disulfide bond correctly. Specifically, such enzymes include protein disulfide isomerase (PDI), which is present in the ER of eukaryotic cells, *Escherichia coli*-derived DsbA, DsbC and the like.

A cell-free protein synthesis system consisting of independently purified factors, which is a suitable cell-free protein synthesis system in the present invention, comprises no or almost no proteins such as the above-described molecular chaperones and PDI. For this reason, the above-described proteins such as molecular chaperones and disulfide isomerases can be added with the optimum choice and concentration. With a conventionally used cell-free protein synthesis system based on cell-extracts, it has been difficult to adjust the system because it inherently comprises the above-described proteins in addition to the proteins necessary for protein synthesis. In this regard, it is shown that a reconstituted cell-free protein synthesis system consisting of independently purified factors is a suitable cell-free protein synthesis system in the present invention.

By translating an mRNA into a polypeptide in the composition of the present invention, a polypeptide encoded by the mRNA can be produced. The present invention also provides such a method for producing a polypeptide.

Production of a polypeptide using the composition of the present invention can be performed by, for example, the steps shown below.

(1) adding a template mRNA to the composition of the present invention, and incubating the same to carry out the translation reaction from the mRNA to the polypeptide;
(2) adding an ice-cold buffer solution to stop the translation reaction; and
(3) recovering the translated polypeptide from the reaction mixture.

When factors that constitute the cell-free protein synthesis system are labeled with a binding partner as described below, the same can be removed from the reaction mixture by capturing the same using a solid phase having a ligand corresponding to the binding partner after completion of the translation reaction. As a result, the produced is polypeptide can easily be recovered from the factors that constitute the cell-free protein synthesis system. When factors that constitute the cell-free protein synthesis system are not labeled with a binding partner, the desired polypeptide can be isolated by previously labeling the desired polypeptide to be produced with a binding partner, and capturing the same using a solid phase carrier having a corresponding ligand after completion of the translation. A protease recognition sequence may be inserted between the desired polypeptide and the binding partner. It is also possible to capture the fusion protein using a solid phase carrier having a ligand corresponding to the binding partner, allow a protease that cleaves the recognition sequence to act, and recover the desired factor. Methods for purifying a factor as described above are publicly known (K. Boon et al., Eur. J. Biochem. (1992) vol. 210, p. 177-183, K. S. Wilson et al., Cell (1998) vol. 92, p. 131-139, Yu-Wen Hwang et al., Arch. Biochem. Biophy. (1997) vol. 348, p. 157-162). Otherwise, using a protein purification technique well known to those skilled in the art (for example, column chromatography and the like), the desired polypeptide can be isolated from the reaction mixture as appropriate.

From the viewpoint of increasing the yield of a polypeptide, it is preferable that the composition of the present invention used in the above-described method for production comprise a release factor and ribosome recycling factor. This is because a release factor and ribosome recycling factor cause the termination of protein synthesis, the release of the translated peptide chain, and the recycling of the ribosome for the initiation of the following translation of the mRNA.

It is preferable that the mRNA to be translated into a polypeptide using the composition of the present invention contain the Shine-Dalgarno (SD) sequence upstream of the initiation codon in order to increase the efficiency of polypeptide production, when a ribosome derived from a prokaryote such as *Escherichia coli*, for example, is utilized in a cell-free protein synthesis system. As with intracellular protein synthesis, the SD sequence, which is a ribosome-binding sequence, upstream of the initiation codon, results in an increased efficiency of the translation reaction.

An mRNA with such a structure can be obtained by, for example, inserting the desired gene into an expression vector harboring a promoter sequence and the SD sequence in 5' UTR, and performing transcription using RNA polymerase. Generally, RNA polymerase recognizes a region comprising a specific sequence called a promoter, and synthesizes an mRNA on the basis of the nucleic acid sequence of following DNA. It is also possible to construct a transcription template having the desired structure by utilizing PCR without using an expression vector (Split-Primer PCR method, Sawasaki et al., PNAS (2002) vol. 99, p. 14652-14657).

The mRNA transcribed by RNA polymerase may be recovered as required, and can be utilized for cell-free protein synthesis using the composition of the present invention. The transcribed mRNA can be recovered by ethanol precipitation after phenol treatment. A commercially available RNA extraction kit such as RNeasy (manufactured by Qiagen) can also be utilized for the recovery of the mRNA.

The above-described DNA itself comprising the gene and the nucleic acid sequences necessary for the transcription and translation can also be used as the template. In this case, using the composition of the present invention comprising RNA polymerase, the DNA is transcribed into an mRNA and the mRNA is translated into a polypeptide.

In the composition of the present invention, the lipopolysaccharide content is suppressed to not higher than a given level; therefore, in a polypeptide produced using the composition of the present invention as well, the lipopolysaccharide content is likewise suppressed. The lipopolysaccharide content in the polypeptide to be obtained is normally $1.0\times10^4$ EU/ml or less, preferably $1.0\times10^3$ EU/ml or less, more preferably $1.0\times10^2$ EU/ml or less, as with the lipopolysaccharide content in the composition of the present invention. As stated above, though lipopolysaccharide possibly facilitates non-specific intermolecular interactions, the lipopolysaccharide content is suppressed in the polypeptide produced using the composition of the present invention. Therefore, using the method for production of the present invention, it is possible to easily produce a polypeptide that allows interactions with other molecules or cells to be evaluated accurately, while suppressing the influences of the non-specific interactions due to contaminating lipopolysaccharide.

Also, because lipopolysaccharide is also called endotoxins and act on human and other cells to express a wide variety of biological activities at cellular level and individual level, it is essential to remove lipopolysaccharide in pharmaceuticals for human administration. Also, in experiments using cultured cells derived from mammals such as humans as well, it is required that reagents from which endotoxins have been removed to the maximum possible extent be used. Using the method for production of the present invention, it is possible to produce a polypeptide with reduced contaminating lipopolysaccharide, that can be used directly, without purification, for experiments using cells, and can be applied to pharmaceuticals and the like. Also, by applying a polypeptide obtained by the method for production of the present invention directly to pharmacological studies at cellular level and individual level, without removing the lipopolysaccharide from the polypeptide, it is possible to conveniently conduct a pharmacological evaluation of the polypeptide under a suppressed influence of lipopolysaccharide.

The present invention also provides ribosome display technology using the above-described composition of the present invention. In the present invention, "ribosome display" is a methodology used to form a tripartite complex consisting of mRNA-ribosome-polypeptide in a cell-free protein synthesis system, and select a nucleic acid that encodes a polypeptide (protein) having a specific function. By binding the complex with the target substance, and separating the complex from other complexes, an mRNA that encodes a polypeptide having the desired binding activity can be obtained. In ribosome display, a cell-free protein synthesis system is utilized; therefore, even a nucleic acid that encodes a polypeptide possessing an activity that injures organisms and cells, or a polypeptide that possibly inhibits the growth of organisms and cells, can be selected.

In the ribosome display of the present invention, by specifically performing the following steps, a nucleic acid that encodes a polypeptide that binds to the target substance is isolated:

(a) a step for translating an mRNA into a polypeptide in the composition of the present invention to form a complex comprising the mRNA and the polypeptide,
(b) a step for contacting the complex formed in (a) with the target substance, and
(c) a step for recovering the complex bound to the target substance, and isolating the mRNA that constitutes the recovered complex or a cDNA thereof as a nucleic acid that encodes the polypeptide that binds to the target substance.

A "nucleic acid" in the present invention refers mainly to a polymer of a deoxyribonucleotide or ribonucleotide. Hence, the nucleic acid is a deoxyribonucleic acid (DNA) or a ribonucleic acid (RNA). Furthermore, the nucleic acids in the present invention can comprise nucleotide derivatives having a non-natural base. The nucleic acids can also comprise peptide nucleic acids (PNAs). As far as the desired genetic information is retained, the constituent unit of the nucleic acid may be any one of these nucleic acids or a blend thereof. Therefore, DNA-RNA hybrid nucleotides are included in the nucleic acids in the present invention. Alternatively, a chimeric nucleic acid generated by joining different nucleic acids, like DNA and RNA, into a single strand is also included in the nucleic acids in the present invention. The structure of any nucleic acid in the present invention is not limited, as far as the desired genetic information is maintained. Specifically, the nucleic acid can assume a structure such as a single strand, double strand, or triple strand. The length of the nucleic acid is at least 3 nucleotides or 6 nucleotides, preferably 9 nucleotides or more. The length of the nucleic acid is normally 10 to 10000 nucleotides or 100 to 5000 nucleotides, for example, 200 to 3000 nucleotides.

The method of the present invention for isolating a nucleic acid that encodes a polypeptide that binds to a target substance comprises a step for first translating an mRNA into a polypeptide in a cell-free protein synthesis system to form a complex comprising the mRNA, a newly generated polypeptide, and a ribosome. In this step, by adding a template mRNA to the composition of the present invention, and carrying out the translation reaction for a given time, a complex consisting of the mRNA, ribosome and a newly generated polypeptide can be formed.

The translation reaction can be carried out by, for example, the following steps:

(1) adding a template mRNA to the composition of the present invention, and incubating the same to carry out the translation reaction from the mRNA to the polypeptide; and
(2) adding an ice-cold buffer solution to stop the translation reaction.

Furthermore, when factors that constitute the cell-free protein synthesis system are labeled with a binding partner, the same can be removed from the reaction mixture by capturing the same using a solid phase having a ligand after completion of the translation reaction. As a result, the produced complex comprising the polypeptide and the mRNA can be easily recovered from other factors that constitute the cell-free protein synthesis system. When factors that constitute the cell-free protein synthesis system are not labeled with a binding partner, a complex comprising the desired polypeptide and the mRNA can be isolated by previously labeling the desired polypeptide to be produced with a binding partner, and capturing the same using a solid phase having a corresponding ligand after completion of the translation. Otherwise, using a protein purification technique well known to those skilled in the art (for example, column chromatography and the like), a complex comprising the desired polypeptide and the mRNA can be isolated from the reaction mixture as appropriate.

From the viewpoint of increasing the yield of the complex comprising the polypeptide and the mRNA, it is preferable that the composition of the present invention used in the above-described method do not comprise a release factor and/or ribosome recycling factor. This is because a nucleic acid that encodes a polypeptide that binds to the target substance can be isolated with high efficiency; without a release factor and/or ribosome recycling factor, the release of the translated peptide chain and the regeneration of the ribosome for the initiation of the following translation of mRNA do not occur, so that a tripartite complex consisting of mRNA-ribosome-polypeptide can be stably formed.

In the ribosome display of the present invention, it is preferable that the mRNA to be translated into a polypeptide in the composition of the present invention comprise the sequences shown below, in order to increase the efficiency of selection by ribosome display.

(1) The SD sequence upstream of the initiation codon (when using an *Escherichia* cold-derived ribosome)
(2) A sequence that encodes a spacer downstream of the desired gene
(3) A partial sequence of SecM downstream of the spacer The containment of the Shine-Dalgarno (SD) sequence, which is a ribosome-binding sequence at upstream of the initiation codon, results in an increased efficiency of the translation reaction as in ordinary protein synthesis when utilizing an *Escherichia coli*-derived ribosome in the cell-free protein synthesis system. Furthermore, in ribosome display, a sequence that encodes a spacer is required to be contained downstream of the desired gene. The spacer prevents steric hindrance between the newly generated polypeptide and the ribosome by providing a sufficient space for the translated polypeptide to be accurately folded outside of the ribosome. Here, without a spacer of sufficient length, the desired polypeptide is unable to go out completely from the ribosome, so that selection by ribosome display cannot be performed efficiently. The spacer consists of at least 20 amino acids, preferably 30 amino acids or more, more preferably 40 amino acids or more in length. Specifically, a partial sequence of the phage gene III and the like can be used. Furthermore, to stabilize the mRNA-ribosome-polypeptide tripartite complex, an mRNA having a sequence that encodes the *Escherichia coli* SecM translation elongation stalling sequence (amino acid residues 148 to 170) placed downstream of the spacer sequence can also be used. This translation elongation stalling sequence has been shown to firmly interact with the peptide tunnel of ribosome (Nakatogawa et al., Cell (2002) vol. 108, p. 629-636), and has been proven to efficiently stop the elongation of the translation when using a reconstituted cell-free protein synthesis system (Nakatogawa et al., Mol. Cell. (2006) vol. 22, p. 545-552).

An mRNA with such a structure can be obtained by, for example, inserting the desired gene into an expression vector harboring a 5' UTR sequence comprising a promoter sequence and the SD sequence, or a 3' terminal spacer sequence, and transcribing the same using RNA polymerase. Generally, RNA polymerase recognizes a region comprising a particular sequence called a promoter, and synthesizes an mRNA on the basis of the nucleic acid sequence of the DNA placed downstream thereof. It is also possible to construct a transcription template having the desired structure by utilizing PCR without using an expression vector (Split-Primer PCR method, Sawasaki et al., PNAS (2002) vol. 99, p. 14652-14657). In this method, a template DNA is constructed by adding a 5' UTR sequence and a spacer sequence to the desired DNA by PCR. In preparing a library of mRNAs from a DNA library, it is unnecessary to clone a DNA into the above-described vector. For this reason, time and labor can be saved.

How to construct a template DNA by PCR is specifically exemplified below.

(1) The DNA region that encodes the desired polypeptide is amplified from an appropriate library and the like by a FOR using a primer comprising a 5' UTR sequence comprising a promoter and the SD sequence and a primer comprising a portion of a spacer sequence.

(2) The amplified DNA is again amplified with the primer for the 5' UTR portion and a primer comprising a spacer portion and the SecM sequence.

By further amplifying the DNA thus constructed as required, and performing transcription using RNA polymerase with the amplified DNA as the template, an mRNA that serves as the template for the translation reaction can be obtained.

The mRNA transcribed by RNA polymerase is recovered as required, and can be utilized for cell-free protein synthesis using the composition of the present invention. The transcribed mRNA can be recovered by ethanol precipitation after phenol treatment. Commercially available RNA extraction kits such as RNeasy (manufactured by Qiagen) can be utilized for recovering the mRNA.

Also, the above-described DNA itself comprising the gene and the nucleic acid sequences necessary for the transcription and translation incorporated in said gene can also be used as the template. In this case, the DNA is transcribed into an mRNA using the composition of the present invention comprising RNA polymerase, and the mRNA is translated into a polypeptide to form the tripartite complex.

In the present invention, a library of nucleic acids can be used as a nucleic acid that encodes a polypeptide. In the present invention, a "library" refers to a population with diversity consisting of a plurality of cloned nucleic acids. A nucleic acid that encodes a protein (polypeptide) having a desired property can be obtained from a library using an in vitro selection system such as ribosome display. The library of nucleic acids in the present invention includes a cDNA library, an mRNA library, and a genomic DNA library. In prokaryotic cells and yeast cells, usually no intron is present in most genes. Therefore, in the case of prokaryotic cells and yeast cells, a genomic DNA library can be utilized to directly screen for a nucleic acid that encodes a protein having the desired property from proteins derived from the cells. In higher eukaryotes such as mammals, conversely, an intron is present in most genes, so that a cDNA library is usually utilized.

The nucleic acid sequences that constitute the library can comprise not only sequences of natural origin, but also artificially introduced sequences. For example, libraries incorporating a mutation are included in the library in the present invention. Alternatively, a library comprising sequences prepared by joining an artificial sequence to a sequence of natural origin is also included in the library in the present invention. Furthermore, a library comprising a completely artificially designed sequence is also included in the library in the present invention.

Proteins encoded by nucleic acids that constitute the library are optionally chosen. Specifically, nucleic acids encoding proteins secreted extracellularly and proteins on the cell membrane, such as antibodies, ligands, adhesion factors, pumps, channels, and receptors, intracellular proteins such as signaling factors, nuclear receptors, and transcription factors, or partial sequences thereof can be utilized for the library. Alternatively, nucleic acids that encode a plurality of kinds of proteins, not limited to a protein with a specific function, can be utilized as a library. Otherwise, nucleic acids that encode a wide variety of random peptides consisting of random amino acid sequences can be utilized as a library. The random peptides comprise peptides differing from each other in terms of amino acid sequence or length, or both.

The method of the present invention comprises a step for contacting a complex comprising an mRNA and a polypeptide with a target substance. In the present invention, a "target substance" refers to a substance to which the desired polypeptide can bind. In other words, a substance to which the polypeptide to be selected from a library binds is a target substance. In the present invention, any substance to which a polypeptide can bind can be utilized as the target substance. The target substances of the present invention include, for example, nucleic acids, polypeptides, organic compounds, inorganic compounds, low-molecular weight compounds, sugar chains, fats, and lipids. More specifically, a substance that functions as an antigen or hapten can be utilized as the target substance. In this case, the desired antibody can be screened for from an antibody library. Alternatively, with a receptor as the target substance, a ligand thereof can be screened for. Also, a membrane fraction of cells that present a target substance such as a receptor can be utilized as the target substance.

Furthermore, by using an antibody and a nucleic acid library that encodes a random peptide library as the target substance and the nucleic acid library, respectively, the epitope of the antibody can be determined. An epitope is a portion of an antigen to which an antibody binds. When the antigen is a protein, a peptide of about 5 to 10 residues can usually serve as an epitope. Determining the epitope for a particular antibody is called epitope mapping. It has already been reported that conventional ribosome display can be applied to epitope mapping (L. C. Mattheakis et al., Proc. Natl. Acad. Sci. USA (1994) vol. 91, p. 9022-9026). It has also already been shown that epitope mapping can be performed even in ribosome display using a reconstituted cell-free protein synthesis system (Osada et al., J. Biochem. (2009) vol. 145, p. 693-700). That is, epitope mapping can be performed on the basis of the present invention.

Conditions for contacting a complex consisting of an mRNA, a ribosome, and a translated polypeptide with a target substance to enable their binding are publicly known except for the use of the composition of the present invention with a reduced lipopolysaccharide content (WO95/11922, WO93/03172, WO91/05058), and can be established without excess burdens by those skilled in the art. To recover the complex bound to the target substance, it is necessary to screen for the complex bound to the target substance from among complexes not bound to the target substance. This is performed according to a known method called panning (Coomber, Method Mol. Biol. (2002) vol. 178, p. 133-145). The basic procedures for panning are as described below.

(1) The complex is contacted with the target substance immobilized on a solid phase carrier. Alternatively, the complex is contacted with the target substance labeled with a binding partner to be captured by a solid phase carrier, after which the target substance bound to the complex is immobilized onto the solid phase carrier.

(2) The complexes not bound to the target substance are removed. For example, the same can be removed by washing.

(3) The complex that has not been removed is recovered.

(4) The processes (1) to (3) are repeated a plurality of times as required.

When repeating the series of steps, it is also possible to amplify the mRNA that constitutes the recovered complex before the step (1). The mRNA can be amplified by, for example, RT-PCR. DNA is synthesized by RT-PCR with the mRNA as the template. The DNA may be transcribed again to an mRNA, and can be utilized for forming the complex. For mRNA transcription, DNA can be inserted into a vector. Alternatively, the structure necessary for the transcription may be joined to DNA to transcribe to mRNA.

Herein, "screening" refers to selecting an entity with the desired property from among substances synthesized by a chemical synthesis, an enzymatic reaction or a combination thereof, substances prepared from extracts of various cells, or naturally occurring substances. "Cloning" refers to isolating a particular gene.

As stated above, in the composition of the present invention, the lipopolysaccharide content is suppressed to not higher than a given level; therefore, in the complex comprising an mRNA and a polypeptide, produced using the composition of the present invention as well, the lipopolysaccharide content is likewise suppressed; the lipopolysaccharide content in the complex is normally $1.0\times10^4$ EU/ml or less, preferably $1.0\times10^3$ EU/ml or less, more preferably $1.0\times10^2$ EU/ml or less, depending on the lipopolysaccharide content in the composition of the present invention. Lipopolysaccharide facilitates the non-specific binding of the above-described complex to the solid phase carrier for immobilizing the target substance, but the complex comprising an mRNA and a polypeptide, produced using the composition of the present invention, has a reduced lipopolysaccharide content. Therefore, using the composition of the present invention, it is possible to suppress the non-specific binding of the tripartite complex consisting of mRNA-ribosome-polypeptide to the solid phase carrier for immobilizing the target substance, and select a nucleic acid that encodes the desired polypeptide with higher accuracy and higher efficiency.

Therefore, in the method of the present invention, it is preferable that the target substance that binds to the polypeptide be bound to a solid phase carrier or labeled with a binding partner to be captured by a solid phase carrier. A material that can bind to and retains the target substance and can be separated from the medium used for the screening can be utilized as the solid phase carrier. The solid phase carrier may be any one capable of binding to the target substance; the solid phase may be in the form of a plate, a rod, particles, or beads. The solid phase carrier can be made of materials that are insoluble in the screening medium such as water or organic solvent. For example, plastics, glass, resins such as polystyrene, gels such as polysaccharides, and metals such as silica, gold thin films, and magnets can be mentioned as materials to be utilized for the solid phase carrier.

In panning, it is preferable that these solid phase carriers be coated with a blocking agent on the surfaces thereof. If the solid phase carrier is not subjected to a blocking agent, components of the cell-free protein synthesis system and the above-described complex bind non-specifically to these solid phase carriers, and they themselves become non-specific antigens in the selection system and possibly interfere with the intended selection of the target substance. The blocking agent is preferably one a contaminated by relatively small amount of RNase or one substantially free from contamination by RNase. Generally, proteins are used as blocking agents. Suitably used proteins include, but are not limited to, blocking proteins contaminated by relatively small amount of RNase (for example, ChemiBLOCKER, Block ACE and the like), Acetylated BSA subjected to RNase inactivation treatment and the like.

Coating of the solid phase carrier with a blocking agent can be achieved by allowing the solid phase carrier to stand in a buffer containing the blocking agent for a time sufficient for the coating (e.g., 30 minutes to 12 hours). The concentration of the blocking agent in the buffer is not particularly limited, as far as coating of the solid phase carrier with the blocking agent is possible; when the blocking agent is a protein, the concentration is normally about 0.1 to 10 (w/v)%.

The target substance binds directly or indirectly to the solid phase carrier. Direct binding refers to, for example, chemical binding or physical adsorption. Indirect binding refers to, for example, binding utilizing a binding partner and a ligand. For example, hydrophilic substances such as proteins are adsorbed to plastic surfaces. This type of binding is called physical adsorption. Therefore, when a protein is the target substance, the same can be bound to the inner wall of a plate or tube made of a plastic by physical adsorption. Alternatively, adsorption of a protein to the solid phase carrier by heat treatment is also included in physical adsorption. The target substance can also be chemically bound to a solid phase carrier. Chemical binding includes, for example, binding via a covalent bond or the like. Specifically, solid phase carriers having a functional group such as the carboxyl group or amino group on the surface thereof are known. A polypeptide, a sugar, a lipid or the like can be bound to these functional groups via a covalent bond. Generally, the bond in chemical binding is stronger than in physical adsorption.

In addition to direct binding such as physical adsorption or chemical binding, the target substance can be indirectly bound to a solid phase carrier. A "binding partner" utilized for the indirect binding refers to one of substances that adhere to each other and labels the target substance. A "ligand" refers to the other of the substances that adhere to each other. Hence, if substances that adhere to each other are written [A] and [B], respectively, the substance [A] that labels the target substance is referred to as a "binding partner", whereas [B] is a "ligand". The relationship among these substances can be expressed by the general formula shown below.

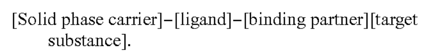
[Solid phase carrier]-[ligand]-[binding partner][target substance].

Provided that the target substance is labeled with a binding partner, a solid phase carrier having a ligand of the binding partner can be utilized. Hence, the target substance can be retained by a solid phase carrier via the binding of the binding partner and a ligand thereof. Shown below are examples of combinations of a binding partner and a ligand thereof that can be utilized in the present invention. His tag and a metal complex such as a nickel complex or a cobalt complex (Bornhorst and Falke, Methods Enzymol. (2000), vol. 326, p. 245-254)

Thioredoxin and PAO (Alejo et al., J. Biol. Chem. (1997) vol. 272, p. 9417-9423)

T7-tag and a monoclonal antibody specific for T7-tag (Dedra et al., J. Bacteriol. (1997) vol. 179, p. 6355-6359)

FLAG peptide tag (Sigma) and an anti-FLAG antibody (Sigma) (Woodring and Garrison, J. Biol. Chem. (1997) vol. 272, 30447-30454)

Staphylococcal Protein A (SPA) and an antibody (IgG) (Nilsson and Abrahmsen, Methods Enzymol. (1990) vol. 185, p. 144-161) Strep-Tag and streptavidin (Skerra and Schmidt, Methods Enzymol. (2000) vol. 326, p. 271-311)

Biotin and avidin (or streptavidin or a derivative thereof) (Alche and Dickinson, Prot. Express. Purif. (1998) vol. 12, p. 138-143).

Therefore, the state wherein the target substance is "labeled with a binding partner" is exemplified by the fact that the target substance is labeled with the binding partner biotin. In this case, the ligand avidin, streptavidin, or derivative thereof is previously immobilized onto a solid phase carrier. By binding biotin and avidin, streptavidin, or a derivative thereof, it is possible to immobilize the target substance onto the solid phase carrier indirectly via biotin. Known derivatives of avidin and streptavidin include Neutravidin (Pierce), Strep-Tactin (IBA) and the like, which can be purchased and used.

A solid phase carrier having the target substance immobilized thereto directly or indirectly can be used in the method of the present invention for isolating a nucleic acid that encodes a polypeptide that binds to the target substance. Alternatively, after the target substance and a polypeptide that binds to the target substance are contacted, the target substance may be captured by a solid phase carrier and isolated. These methods are applicable to the present invention, whatever of the above-described methods is used.

In phage display, steps for eluting the phage that presents a polypeptide that binds to the target substance and infecting the same to *Escherichia coli* to allow the phage to proliferate are required after the phage that has not bound to the target substance has been removed by washing. When panning is repeated, it is necessary to repeat the steps of infection to *Escherichia coli* and phage proliferation as well. However, in the present invention, these steps are not needed. Even when panning is repeated, a cDNA may be synthesized from the mRNA in the complex that has bound to the target substance, and amplified by PCR, after which a transcription/translation reaction may be again carried out to form an mRNA-ribosome-polypeptide tripartite complex. Therefore, the method according to the present invention allows screening to be performed more quickly than a method based on phage display.

After the complex that presents the desired polypeptide is selected, the sequence of the nucleic acid that encodes the polypeptide can be identified. At the stage when the complex is selected, the nucleic acid that encodes the polypeptide is an mRNA. By synthesizing a cDNA using a reverse transcriptase with this mRNA as the template, and reading the nucleic acid sequence using a sequencer, the nucleic acid sequence thereof can be determined. These techniques are publicly known.

Also, the present invention provides a kit for isolating a nucleic acid that encodes a polypeptide that binds to a target substance, comprising the following components:

(1) the composition of the present invention, and (2) a solid phase carrier for immobilizing the target substance.

The kit of the present invention can further comprise a blocking agent for coating the surface of the solid phase carrier. The blocking agent is preferably a protein.

The kit of the present invention may further comprise a library of nucleic acids to be used in performing the ribosome display of the present invention.

The kit of the present invention may further comprise a target substance to be used in performing ribosome display of the present invention.

By performing the above-described ribosome display of the present invention using the kit of the present invention, it is possible to efficiently isolate a nucleic acid that encodes a polypeptide that binds to the target substance.

The definitions for the various terms concerning the kit of the present invention and modes of their embodiments are as described above.

All the reference documents, including publications, patent documents and the like, cited herein are incorporated herein by reference to the extent that they are individually specifically cited for reference, and that all the teachings thereof are specifically described.

The present invention is hereinafter described more specifically by means of the following Examples, by which, however, the present invention is not limited in any way.

EXAMPLES

Example 1

Removal of Lipopolysaccharide from Proteinous Factor Solution

Lipopolysaccharide was removed from already purified proteinous factors with reference to Reichelt et al., (2006) Protein Expr Purif., vol. 46, p. 483. Specifically, this process was performed as described below. A solution containing 0.5 to 1 mg of each of His-tagged protein factors independently purified according to Japanese Patent 4061043 was diluted to 450 μl with Binding Buffer (50 mM Tris-HCl pH 8, 500 mM NaCl, 20 mM imidazole, 7 mM 2-mercaptoethanol). Added to the diluted protein solution was 100 μl of 50% (v/v) Ni-Sepharose FF (GE Healthcare) suspension; after mixing at 4° C. for 1 hour, the mixture was applied to MicroBiospin column (Bio-Rad). The resin was washed with 500 μl of Binding Buffer supplemented with 0.1% Triton X-114 10 times, and with Binding Buffer 5 times, after which the protein was eluted with 200 μl of Elution Buffer (50 mM Tris-HCl pH 8, 500 mM NaCl, 400 mM imidazole, 7 mM 2-mercaptoethanol). The eluted solution was concentrated to 50 μl or less using an ultrafiltration apparatus (AmiconUltra-0.5 (Millipore)), after which 450 μl of Stock Buffer (20 mM HEPES-KOH pH 7.6, 100 mM KCl, 7 mM 2-mercaptoethanol, 30% glycerol) was added, and concentrating process was performed again. This process was repeated 4 times to replace Elution Buffer with Stock Buffer. The concentration of the protein was determined by the Bradford method (Protein Assay, Bio-Rad).

Example 2

Removal of Lipopolysaccharide from Ribosome Using Cholic Acid (Treatment A)

Ribosome was prepared from *Escherichia coli* using a method disclosed in JP-A-2008-271903 with the partial modification as below. Sodium cholate was added to the eluted solution from hydrophobic column to make 0.5% (w/v), and the mixture was incubated at 4° C. for 1 hour, after which the mixture was gently placed on Sucrose Buffer (20 mM HEPES-KOH pH 7.6, 10 mM $Mg(OAc)_2$, 30 mM $NH_4Cl$, 30% sucrose, 7 mM 2-mercaptoethanol) and centrifuged at 4° C. at 100,000×g overnight, and the ribosome was recovered as a precipitate. The precipitate was dissolved in 70S Buffer (20 mM HEPES-KOH pH 7.6, 6 mM $Mg(OAc)_2$, 30 mM KCl, 7 mM 2-mercaptoethanol), and the absorbance at 260 nm was measured to determine the concentration of the ribosome solution.

Example 3

Removal of Lipopolysaccharide from Ribosome Using Triton X-114 (Treatment B)

Ribosome was prepared from *Escherichia coli* by a method disclosed in JP-A-2008-271903. 900 μl of ice-cold 70S Buffer supplemented with 1% Triton X-114 was added to 100 μl of about 30 μM ribosome fraction prepared, and they were gently mixed. The mixture was allowed to stand for 5 minutes, and then further allowed to stand at 30° C. in an incubator for 5 minutes. The turbid mixture was centrifuged at room temperature at 20,000×g for 5 minutes to separate into two phases. About 900 μl of the upper phase was recovered and transferred onto ice, after which 100 μl of ice-cold 70S Buffer supplemented with 10% Triton X-114 was added, and they were gently mixed. The mixture was allowed to stand on ice for 5 minutes, and then further allowed to stand at 30° C. in an incubator for 5 minutes. The turbid mixture was centrifuged at room temperature at 20,000×g for 5 minutes to separate into two phases. This process was repeated a total of 5 times, whereby about 800 μl of the upper phase was finally recovered. The recovered fraction containing the ribosome was gently placed on Sucrose Buffer and centrifuged at 4° C. at 100,000×g overnight, and the ribosome was recovered as a precipitate. The precipitate was dissolved in 70S Buffer, and the absorbance at 260 nm was measured to determine the concentration of the ribosome solution.

Example 4

Removal of Lipopolysaccharide from tRNA Mixture

A commercially available *Escherichia coli* tRNA mixture (manufactured by Roche) was dissolved in RNase-free water; the absorbance at 260 nm was measured, and tRNA solution at a concentration of about 800 $A_{260}$/ml was prepared. To 100 μl of the prepared tRNA solution, 900 μl of ice-cold 50 mM Tris-HCl pH 8, 1% Triton X-114 solution was added, and they were gently mixed. The mixture was allowed to stand on ice for 5 minutes, and then further allowed to stand at 30° C. in an incubator for 5 minutes. The turbid mixture was centrifuged at room temperature at 20,000×g for 5 minutes to separate two phases. About 900 μl of the upper phase was recovered and transferred onto ice, after which 100 μl of ice-cold 50 mM Tris-HCl pH 8, 10% Triton X-114 solution was added, and they were gently mixed. After the mixture was allowed to stand on ice for 5 minutes, the same was further allowed to stand at 30° C. in an incubator for 5 minutes. The turbid mixture was centrifuged at room temperature at 20,000×g for 5 minutes to separate into two phases. This process was repeated a total of 5 times, whereby about 800 μl of the upper phase was finally recovered. The tRNA was recovered from the recovered upper layer as a precipitate by ordinary ethanol precipitation and dissolved in RNase-free water. The absorbance at 260 nm was measured to determine the concentration of the tRNA solution. With this process, the tRNA recovery rate was about 80%.

Example 5

Preparation of Protein Synthesis Reaction Mixture

A protein synthesis reaction mixture was prepared using factors treated with Triton X-114, according to the composition and concentration shown in Shimizu et al., (2005) Methods, vol. 36, p. 299-304. For control, a synthesis reaction mixture with non-treated factors was prepared in the same manner.

Example 6

Quantitation of Lipopolysaccharide

Figure 2:
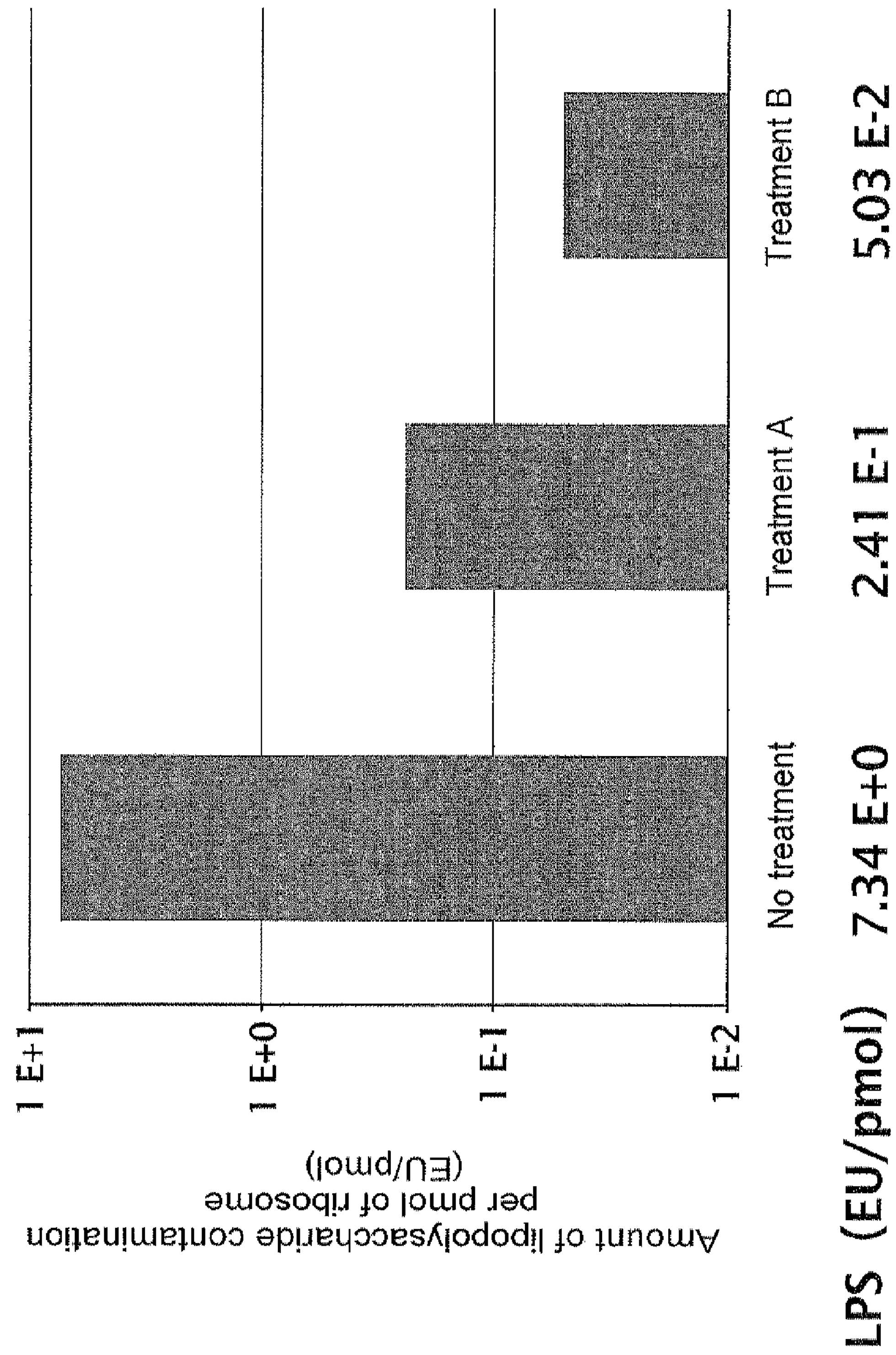
FIG. 2 shows the amounts of contaminating lipopolysaccharide in the ribosome. Shown are the amounts of contaminating lipopolysaccharide in a ribosome not treated with a surfactant (non-treated), a ribosome treated with cholic acid (treatment A), and a ribosome treated with Triton X-114 (treatment B).
Figure 3:
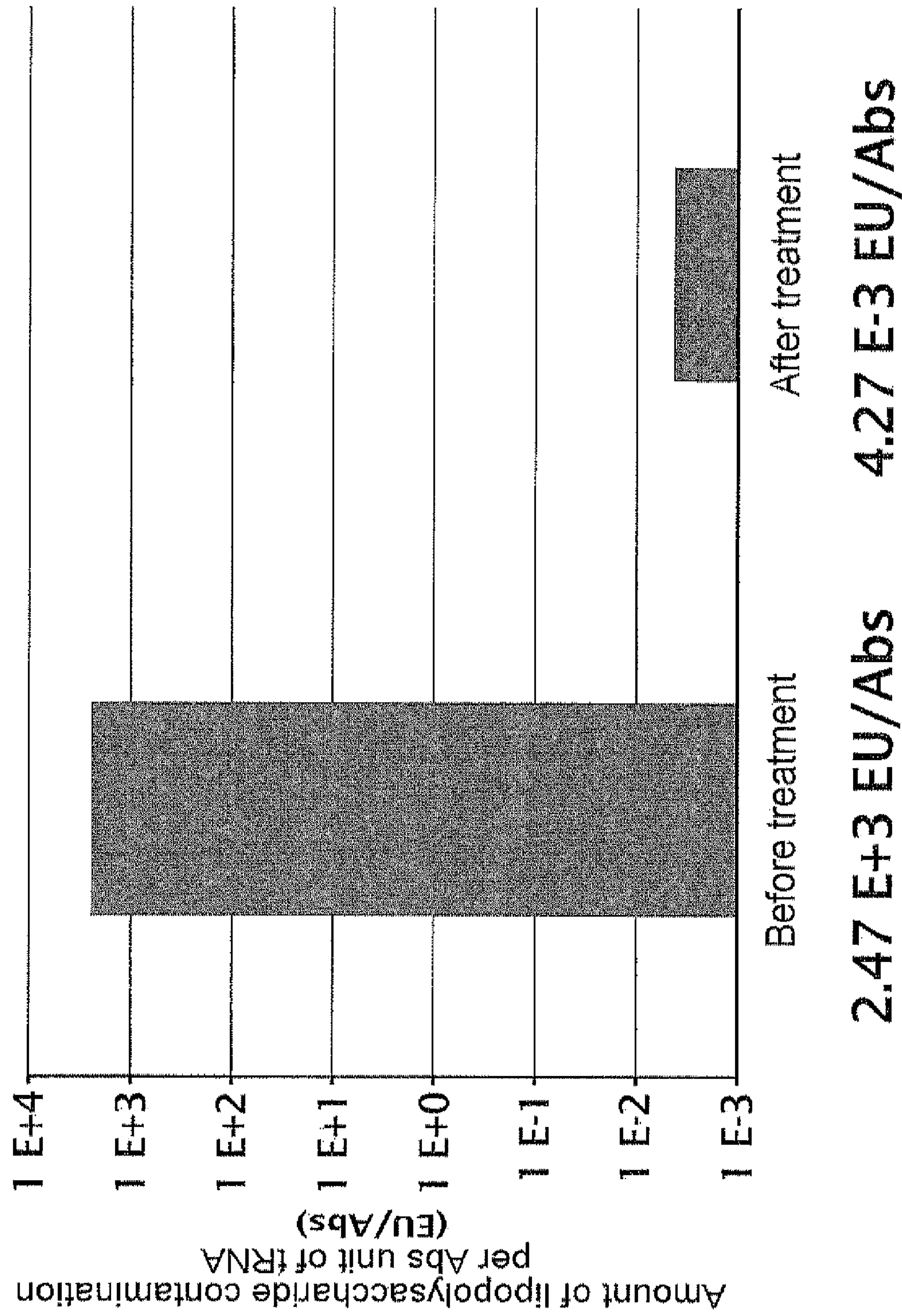
FIG. 3 shows the amounts of contaminating lipopolysaccharide in the tRNA mixture. Shown are the amounts of contaminating lipopolysaccharide in the tRNA mixture before and after removal treatment of lipopolysaccharide.
Figure 4:
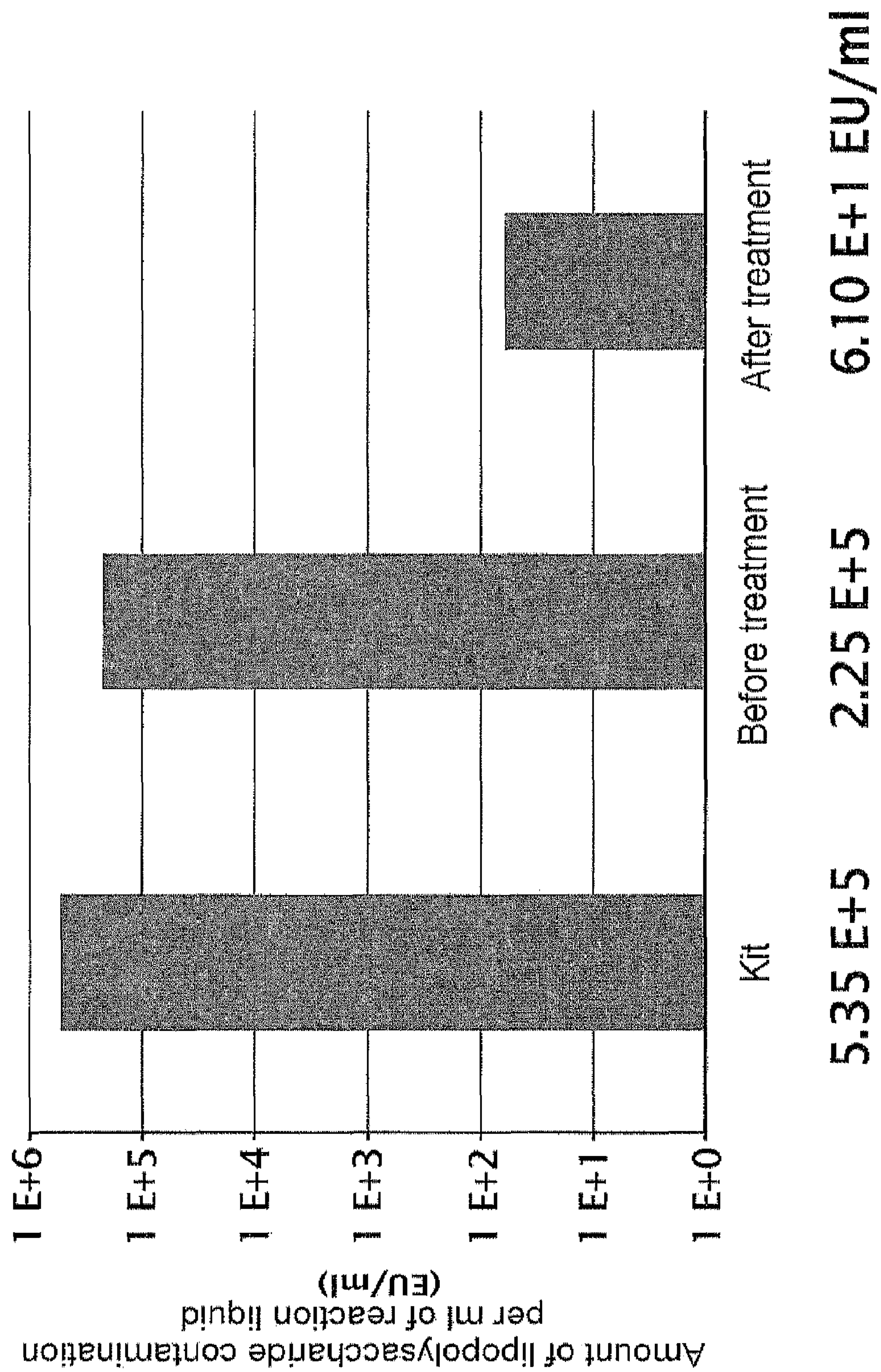
FIG. 4 shows the amounts of contaminating lipopolysaccharide in the reconstituted cell-free protein synthesis systems. Shown are the amounts of contaminating lipopolysaccharide in protein synthesis reaction mixture prepared by mixing factors not subjected to lipopolysaccharide removal treatment, and a protein synthesis reaction mixture prepared by mixing the factors subjected to the lipopolysaccharide removal treatment. Also shown is the amount of contaminating lipopolysaccharide in the protein synthesis reaction mixture contained in the PURExpress kit manufactured by New England Biolabs.

The amount of lipopolysaccharide contaminated in each of protein factors (FIG. 1), ribosomes (FIG. 2), tRNAs (FIG. 3), and synthesis reaction mixtures (FIG. 4) was measured using a commercially available endotoxin assay reagent (Limulus Color KY Test Wako, Wako Pure Chemical) according to the attached manual. In measuring the amount of contaminating lipopolysaccharide in each protein synthesis reaction mixture, the amount of contaminating lipopolysaccharide in the PURExpress kit (New England Biolabs) was also measured for control. Lipopolysaccharide concentrations were calculated as endotoxin unit (EU) values on the basis of the concentrations of the reference standards of endotoxin attached to the assay reagent.

As a result, for each of the protein factors (FIG. 1), ribosomes (FIG. 2), tRNAs (FIG. 3), and protein synthesis reaction mixtures (FIG. 4), it was confirmed that the lipopolysaccharide content decreased with the above-described process.

Example 7

Synthesis of Dihydrofolate Reductase (DHFR)

The *Escherichia coli* DHFR protein was synthesized from the DNA that encodes the same according to Japanese Patent 4061043 and Shimizu et al., (2005) Methods, vol. 36, p. 299-304, using the protein synthesis reaction mixture prepared in Example 4. After the synthesis, each reaction mixture was subjected to SDS-PAGE, after which the gel was stained with SyproOrange (Invitrogen), and protein bands were detected using a fluorescence imager (FLA-3000 (FujiFilm)).

Figure 5:
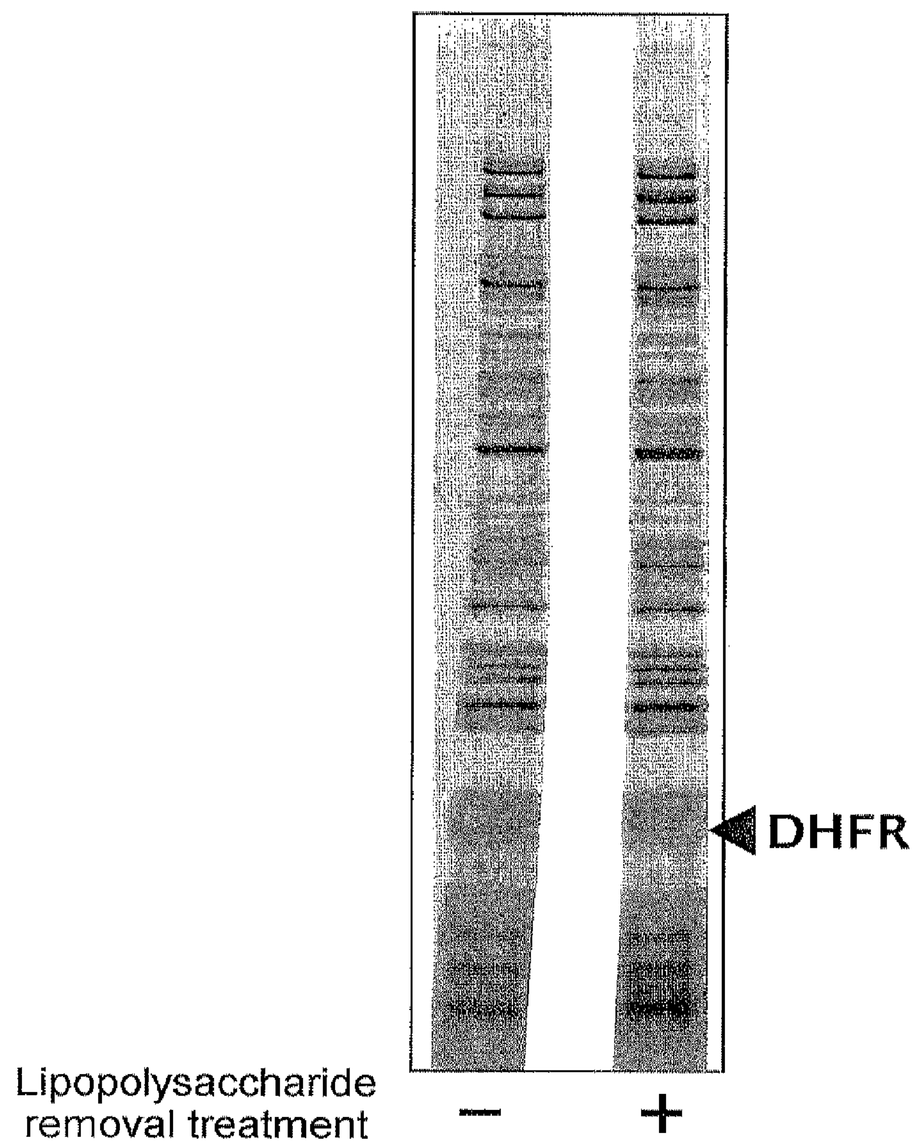
FIG. 5 shows the results of protein synthesis reaction. Reaction mixture in which *Escherichia coli* dihydrofolate reductase (DHFR) was synthesized using the protein synthesis reaction mixture not subjected to the lipopolysaccharide removal treatment or the protein synthesis reaction mixture subjected to the lipopolysaccharide removal treatment were applied to electrophoresis and stained with SyproOrange. The band of the synthesized DHFR protein is indicated by the arrow.

As a result, as shown in FIG. 5, it was shown that the desired protein could be synthesized even when using the protein synthesis reaction mixture subjected to the lipopolysaccharide removal treatment.

Example 8

Ribosome Display

1. Preparation of Domain Antibody Gene for Ribosome Display

An anti-Erk2 antibody gene previously selected from a commercially available human VH domain antibody phage display library (Human Domain Antibody Library: DNAFORM) was reconstructed for ribosome display. Specifically, after PCR amplification with KOD-Plus-DNA Polymerase (TOYOBO) using the 5' primer of FLAG_Dab-F (SEQ ID NO:1: ATGGACTATAAAGATGACGATGACAAAGGCcaggtgcagctgttggagtctgggggagg), which comprise a FLAG tag sequence at the N-terminus, and the 3' primer of myc(E1)His-R (SEQ ID NO:2: gatggtgacctccgctgccaccgaattccagatcctcttctgagatgagtttttgttc), which comprises a C-Myc tag sequence at the C-terminus (denaturation: 94° C., 10 seconds, annealing: 57° C., 30 seconds, extension: 68° C., 60 seconds, 25 cycles), the gene was purified using the QIAquick PCR Purification Kit (QIAGEN). A 5' UTR sequence comprising the T7 promoter and the SD sequence with a FLAG sequence added to the 3' terminus, which are needed in performing ribosome display, in addition to FLAG sequence was also synthesized chemically (FASMAC). 5' UTR (SEQ ID NO:3: gaaattaatacgactcactatagggagaccacaacggtttccctctagaaataattttgttt aactttaagaaggagatataccaatggactataaagatgacgatgacaaa)

The gene III (g3p) portion fragment of the M13 phage was amplified by PCR with KOD-Plus-DNA Polymerase (TOYOBO) from the M13KO7 phage genome as the template, using the primer g3p (SEQ ID NO:4: GAATATCAAGGCCAATCGTCTGAC) and the primer g3p-SecMstop (SEQ ID NO:5: CTCGAGTTATTCATTAGGTGAGGCGTTGAGGGCCAGCACGGATGCCTTGCGCCTGGCTTATC CAGACGGGCGTGCTGAATTTTGCGCCGGAAACGTCACCAATGAAAC) (denaturation: 94° C., 10 seconds, annealing: 57° C., 30 seconds, extension: 68° C., 60 seconds, 25 cycles), and then purified using the QIAquick PCR Purification Kit (QIAGEN).

1 pmol of each of the synthesized 5' UTR, the purified anti-Erk2 domain antibody gene and g3p gene fragment, 10 pmol of a 5' primer (SEQ ID NO:6: GAAATTAATACGACTCACTATAGGGAGACCACAACGCTTTCCCTCTAG), 10 pmol of the 3' primer SecMstop (SEQ ID NO:7: GGATTAGTTATTCATTAGGTGAGGCGTTGAGG), and 1 µl of KOD-Plus-DNA polymerase were added to the reaction mixture to carry out a PCR reaction (denaturation: 94° C., 10 seconds, annealing: 57° C., 30 seconds, extension: 68° C., 60 seconds) in 10 cycles. After a band of a product containing all the fragments linking together was identified by electrophoresis using 1% agarose gel; the desired band was excised and purified using the MiniElute Gel Extraction Kit (QIAGEN) to give the gene for ribosome display.

2. In vitro Transcription

An mRNA was synthesized from 1 µg of the purified anti-Erk2 domain antibody gene for ribosome display using an in vitro transcription kit (RiboMAX™ Large Scale RNA Production System-T7 (Promega)), and purified using the RNeasy mini kit (QIAGEN).

3. In vitro Translation Using Cell-free Protein Synthesis Reaction Mixtures 1 pmol of the mRNA and 1 µM of ribosome were added to 10 µl of each of the protein synthesis reaction mixture prepared in Example 4 (a mixture wherein only tRNA and ribosome have been treated with Triton X-114, a mixture wherein all factors have been subjected to lipopolysaccharide removal treatment, and a non-treated mixture), and the mixture was incubated at 37° C. for 30 minutes. 250 µl of ice-cold reaction stop solution (50 mM Tris-HCl pH 7.5, 150 mM NaCl, 50 mM $Mg(OAc)_2$, 0.5% Tween 20, 10 mg/ml *Saccharomyces cerevisiae* total RNA (Sigma)) was added to stop the reaction.

4. Purification of mRNA-ribosome-protein Complex (Ribosome Display Complex)

The FLAG M2 beads (5 µl of slurry, Sigma) was twice washed with 500 µl of Wash buffer (50 mM Tris-HCl pH 7.5, 150 mM NaCl, 50 mM $Mg(OAc)_2$, 0.5% Tween 20, 10 mg/ml *Saccharomyces cerevisiae* total RNA (Sigma)), after which each translation reaction mixture was added to the recovered FLAG M2 beads, and stirred by rotation at 4° C. for 1 hour. The supernatant was discarded using the MicroSpin (registered trademark) column (manufactured by GE Healthcare); 200 µL of Wash buffer was added to the recovered FLAG M2 beads, and stirred by rotation at 4° C. for 5 minutes. After this washing process was repeated 10 times, 100 µl of FLAG peptide Elution buffer (50 mM Tris-OAc, pH 7.5, 150 mM NaCl, 50 µg of a FLAG peptide (Sigma)) was added to the recovered FLAG M2 beads, and the mixture was allowed to stand at 4° C. for 15 minutes. Here, the molecules forming the ribosome display complex were released from the FLAG M2 beads by the antigen elution with FLAG peptide. The supernatant was recovered using the MicroSpin (registered trademark) column (manufactured by GE Healthcare Company) to give the ribosome display complex solution. An 1 µl aliquot was stored at −20° C. for RT-PCR.

5. In vitro Selection

The Dynabeads MyOne Streptavidin Cl magnetic beads (5 µl of slurry, Invitrogen) were preblocked with 200 µl of each of 1xChemiBLOCKER (Millipore), 4% Block ACE (DS Pharma Biomedical), and 0.1% Acetylated BSA (Sigma), diluted with a Blocking buffer (50 mM Tris-HCl pH 7.5, 150 mM NaCl, 15 mM $Mg(OAc)_2$), by overnight rotation stirring at 4° C. The blocked magnetic beads were washed with 500 µl of Wash buffer 3 times; a solution containing the purified ribosome display complex was added to the washed magnetic beads, and stirred by rotation at 4° C. for 1 hour. After the supernatant was discarded using the Magnetic Particle Concentrator, the recovered magnetic beads were washed with 100 µl of Wash buffer. After this process was repeated 16 times, EDTA Elution buffer (50 mM Tris-HCl pH 7.5, 150 mM NaCl, 50 mM EDTA) was added to the recovered magnetic beads, and the mixture was allowed to stand at room temperature for 15 minutes, whereby the mRNA was released from the magnetic beads. The supernatant was recovered using the Magnetic Particle Concentrator, and the mRNA was purified using RNeasy MiniElute Cleanup kit (QIAGEN).

6. Quantitation of the Amount of mRNA Recovered

Figure 6:
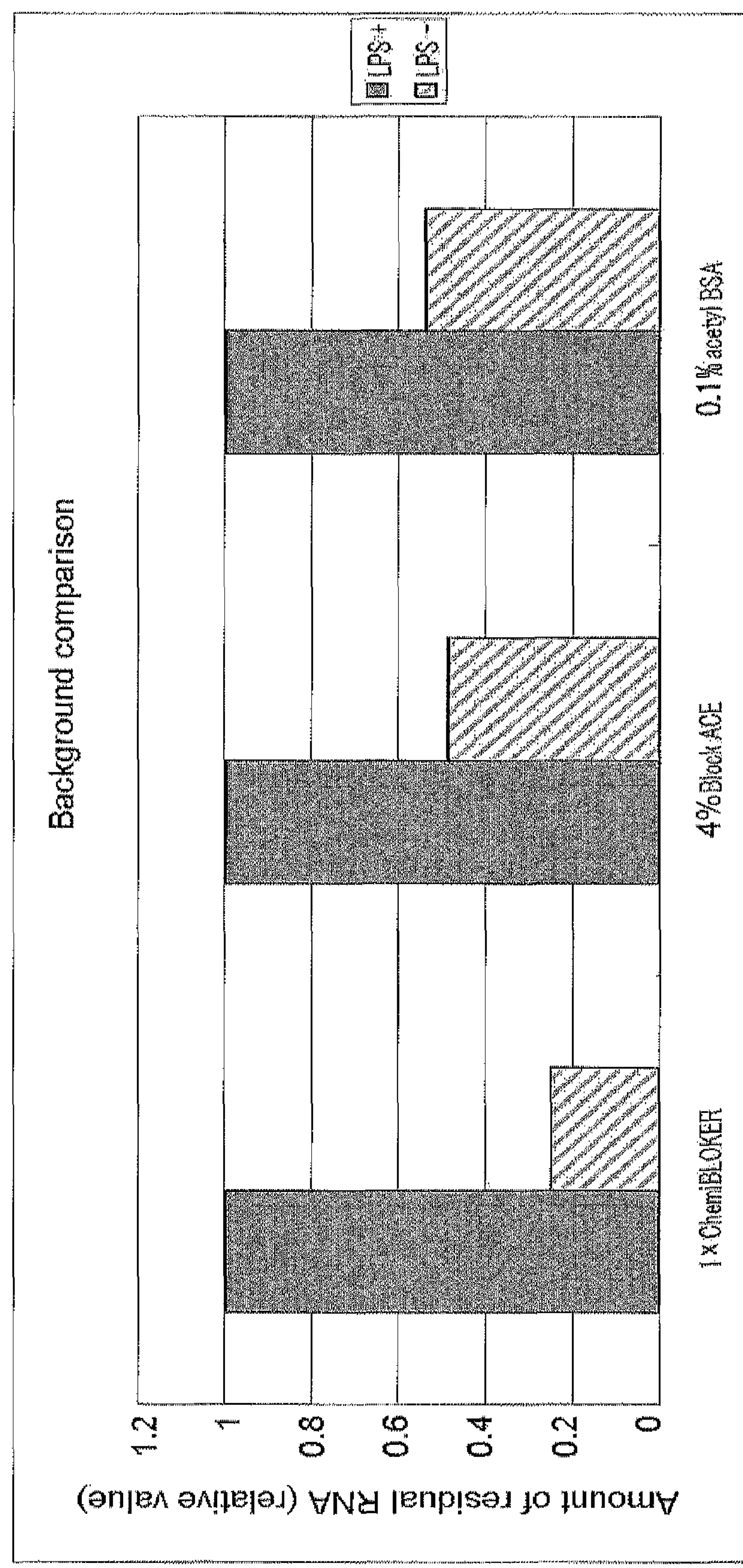
FIG. 6 shows the amounts of lipopolysaccharides and the residual amounts of background mRNA in ribosome display. A comparison of the residual amounts of background mRNA non-specifically adsorbed to magnetic beads surface-coated with three kinds of proteinous blocking agents (ChemiBLOKER, Block ACE, Acetylated BSA) before and after the lipopolysaccharide removal treatment. The vertical axis indicates the relative values of the amount of background mRNA non-specifically adsorbed to the magnetic beads and the amount of mRNA from the mRNA-ribosome-polypeptide tripartite complex purified using a FLAG M2 beads.

After the process of in vitro selection, a reaction mixture comprising 1 µl of the recovered mRNA solution, the primer FLAG-(G) (SEQ ID NO:8: ATGGACTATAAAGATGACGATGACAAAGG), the primer Dab__216-97__335R (SEQ ID NO:9: gacactaatgcctgatacccactctagacc), and the RNA-direct SYBR Green Realtime PCR Master Mix (TOYOBO), was prepared, the amount of mRNA recovered from FLAG peptide elution (Example 7-4) and EDTA elution (Example 7-5) was m quantified according to the standard protocol for SYBR Green assay using LightCycler (Roche). FIG. 6 shows the comparison of the amounts of remaining background mRNA non-specifically adsorbed to magnetic beads blocked with 3 kinds of proteinous blocking agents of different properties, that is, ChemiBLOCKER, which consists of non-animal protein components, Block ACE, which consists of milk protein components, and Acetylated BSA, which consists of a single protein, obtained before and after lipopolysaccharide removal treatment. The vertical axis indicates the relative values of the amount of mRNA non-specifically adsorbed to the magnetic beads and the amount of mRNA from the mRNA-ribosome-polypeptide tripartite complex purified using the FLAG M2 beads. As a result, the amount of the background mRNA decreased by about 25% with ChemiBLOCKER and by about 50% with Block ACE and acetylated BSA, after the lipopolysaccharide removal treatment. This result shows that the more aggressively removing lipopolysaccharide from the protein synthesis reaction mixture can suppress the non-specific adsorption of the ribosome display complex to the proteins, and thereby ribosome display will be performed efficiently.

Example 9

Influences on Human-derived Cells

Figure 7:
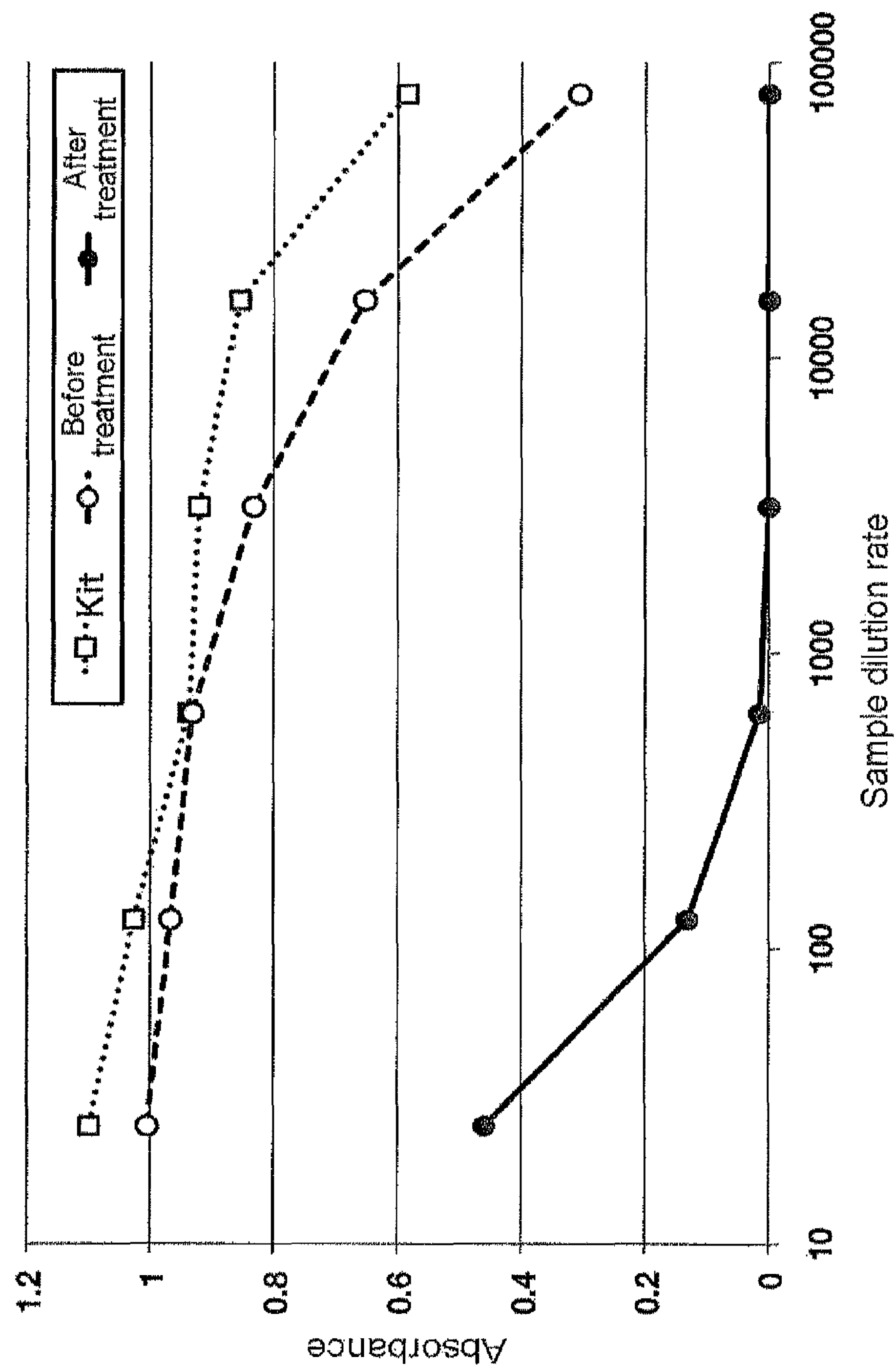
FIG. 7 shows the influences of protein synthesis reaction mixture on cultured cells. A reporter assay was performed using cells cultured in a medium supplemented with serial dilutions of the protein synthesis reaction mixture prepared by mixing factors not subjected to the lipopolysaccharide removal treatment (before treatment), the protein synthesis reaction mixture prepared by mixing the factors subjected to the lipopolysaccharide removal treatment (after treatment), and the protein synthesis reaction mixture contained in the PURExpress kit manufactured by New England Biolabs. Color development by secreted alkaline phosphatase, which is expressed in the presence of lipopolysaccharide, was measured by the absorbance at 630 nm, and is showed as values obtained by subtracting background values.

Influences on cultured cells were checked using the HEK-Blue LPS Detection Kit (Invivogen). This assay kit makes it possible to measure the amount of contaminating lipopolysaccharide by a color developing reaction of the culture medium using cultured cells that express the secreted alkaline phosphatase when the sample contains lipopolysaccharide. The amount of contaminating lipopolysaccharide was measured according to the manual for the assay kit, using as samples in 5-fold serial dilutions of the protein synthesis reaction mixture mixed with factors not subjected to lipopolysaccharide removal treatment, the protein synthesis reaction mixture mixed with factors subjected to the removal treatment, and PURExpress kit manufactured by New England Biolabs. It was shown that with the protein synthesis reaction mixture before the lipopolysaccharide removal treatment, and with the commercially available kit, the cells responded even when a 100,000-fold diluted reaction mixture was added, whereas with the reaction mixture subjected to the lipopolysaccharide removal treatment, the cells became nearly non-responsive to a 500-fold diluted reaction mixture (FIG. 7).

Industrial Applicability

According to the present invention, a composition possessing cell-free protein synthesis activity with reduced contamination of lipopolysaccharide, and a method for producing a protein using the same are provided. A protein with reduced contamination of lipopolysaccharide can be obtained using the composition and method for protein production of the present invention. Furthermore, when ribosome display is performed using the composition and method for protein production of the present invention, the background that is caused by non-specific binding is reduced, so that a nucleic acid that encodes the desired polypeptide can be selected with high accuracy and high efficiency.

The invention claimed is:

1. A composition that possesses cell-free protein synthesis activity and that comprises an independently purified initiation factor, an independently purified elongation factor, an independently purified aminoacyl-tRNA synthetase, an independently purified ribosome, an independently purified amino acid, an independently purified nucleoside triphosphate, and an independently purified tRNA, wherein the initiation factor, the elongation factor, the aminoacyl-tRNA synthetase, and the ribosome each were purified from a Gram-negative bacteria, wherein the composition has a ribosome concentration of 0.01- 50 μM, wherein the independently purified ribosome is a ribosome with a reduced lipopolysaccharide content, obtained by a washing step using a buffer solution comprising a surfactant, wherein the independently purified ribosome has a lipopolysaccharide concentration of 0.5 EU per pmol of ribosome or less, and wherein the composition does not comprise any release factors.

2. The composition according to claim 1, wherein the independently purified ribosome is a ribosome with a reduced lipopolysaccharide content, obtained by a method comprising the following steps:

(I) mixing a surfactant and a ribosome contaminated with lipopolysaccharide, (II) warming the obtained mixture to a temperature not lower than the clouding point of the surfactant, (III) centrifuging the warmed mixture to achieve phase separation, and (IV) isolating the phase containing the ribosome to obtain a ribosome with a reduced lipopolysaccharide content.

3. The composition according to claim 1, wherein the surfactant comprises one or two or more surfactants selected from the group consisting of polyoxyethylene sorbitan alkyl ethers, polyoxyethylene alkyl ethers, polyoxyethylene octylphenyl ethers, alkylglucosides, N-gluco-N-methyl alkanamides, bile salts, amine oxides, and alkyl-N,N-dimethylammoniopropane sulfonates.

4. The composition according to claim 1, wherein the composition further comprises methionyl-tRNA transformylase and 10-formyl 5,6,7,8-tetrahydrofolate.

5. The composition according to claim 1, wherein the Gram-negative bacteria is *Escherichia coli*.

6. The composition according to claim 1, consisting of the independently purified factors.

7. The composition according to claim 1, which is for use in ribosome display.

8. A kit for isolating a nucleic acid that encodes a polypeptide that binds to a target substance, comprising the following constituents:

(1) the composition according to claims 1, and (2) a solid phase carrier for immobilizing the target substance.

9. A method for producing a polypeptide, comprising translating an mRNA into a polypeptide in the composition according to claim 1.

10. A method for isolating a nucleic acid that encodes a polypeptide that binds to a target substance, comprising the following steps:

(a) translating an mRNA into a polypeptide in the composition according to claim 1 to form a complex comprising the mRNA and the polypeptide, (b) contacting the complex formed in (a) with the target substance, and (c) recovering the complex bound to the target substance, and isolating the mRNA that constitutes the recovered complex or a cDNA thereof as a nucleic acid that encodes a polypeptide that binds to the target substance.

11. The method according to claim 10, wherein the mRNA comprises a stop codon on the 3'-terminus of the polypeptide-coding sequence.

12. The method according to claim 10, wherein the target substance is bound to a solid phase or labeled with a binding partner to be captured by a solid phase.

* * * * *